US011498978B2

(12) United States Patent
Kristensen et al.

(10) Patent No.: US 11,498,978 B2
(45) Date of Patent: Nov. 15, 2022

(54) YKL-40 ANTIBODY

(71) Applicant: BIO-Y A/S, Helsingør (DK)

(72) Inventors: Peter Kristensen, Tranbjerg (DK); Peter Minor, København (DK)

(73) Assignee: BIO-Y A/S, Helsingør (DK)

( * ) Notice: Subject to any disclaimer, the term of this patent is extended or adjusted under 35 U.S.C. 154(b) by 164 days.

(21) Appl. No.: 16/867,050

(22) Filed: May 5, 2020

(65) Prior Publication Data
US 2021/0347912 A1 Nov. 11, 2021

(51) Int. Cl.
C07K 16/40 (2006.01)

(52) U.S. Cl.
CPC .......... *C07K 16/40* (2013.01); *C07K 2317/21* (2013.01); *C07K 2317/52* (2013.01); *C07K 2317/565* (2013.01); *C07K 2317/76* (2013.01)

(58) Field of Classification Search
None
See application file for complete search history.

(56) References Cited

FOREIGN PATENT DOCUMENTS

| WO | 2006/089549 A1 | 8/2006 |
| WO | 2010/033913 A1 | 3/2010 |
| WO | 2018/129261 A1 | 7/2018 |
| WO | 2019/040685 A1 | 2/2019 |
| WO | 2019/060675 A1 | 3/2019 |

OTHER PUBLICATIONS

Schroeder et al. (J Allergy Clin Immunol 2010, 125:S41-S52).*
Lloyd et al. Protein Engineering, Design & Selection 2009, 22:159-168.*
Rudikoff et al. (Proc Natl Acad Sci USA 1982 vol. 79 p. 1979).*
MacCallum et al. (J. Mol. Biol. 1996 262, 732-745).*
Pascalis et al. (The Journal of Immunology (2002) 169, 3076-3084).*
Casset et al. (BBRC 2003, 307:198-205).*
Vajdos et al. (J. Mol. Biol. (2002) 320, 415-428).*
Chen et al. (J. Mol. Bio. (1999) 293, 865-881).*
Wu et al. (J. Mol. Biol. (1999) 294, 151-162).*
Padlan et al. (PNAS 1989, 86:5938-5942).*
Lamminmaki et al. (JBC 2001, 276:36687-36694).*
Piche-Nicholas et al. MABS 2018, 10:81-94.*

Baronzio, G. et al., Overview of Methods for Overcoming Hindrance to Drug Delivery to Tumors, with Special Attention to Tumor Interstitial Fluid, Frontiers in Oncology, 5, Article 165, Jul. 23, 2015, 17 pages.
Christ, D. Repertoires of aggregation-resistant human antibody domains, Protein Engineering, Design and Selection, 20(8): 413-416, Aug. 24, 2007.
Faibish, M. et al., A YKL-40-neutralizing antibody blocks tumor angiogenesis and progression: a potential therapeutic agent in cancers, Mol Cancer Ther., 10(5):742-751, 2011.
Francescone, R. et al., Tumor-derived mural-like cells coordinate with endothelial cells: role of YKL-40 in mural cell-mediated angiogenesis, Oncogene, 33:2110-2122, 2014.
Geng, B. et al., Chitinase 3-like 1-CD44 interaction promotes metastasis and epithelial-to-mesenchymal transition through ß-catenin/Erk/Akt signaling in gastric cancer, J Exp Clin Cancer Res, 37, Article No. 208, 2018, 20 pages.
Kang, H. et al., Cancer Cell Glycocalyx and Its Significance in Cancer Progression, International journal of Molecular Sciences, 19(9), 2484, 2018, 23 pages.
Libreros, S. et al., Induction of proinflammatory mediators by CHI3L1 is reduced by chitin treatment: decreased tumor metastasis in a breast cancer model, International Journal of Cancer, 131(2): 377-86, 2012.
Lu, L. et al., Antibody-modified liposomes for tumor-targeting delivery of timosaponin AIII, International Journal of Nanomedicine, 13, 1927-1944, 2018.
Mandrup, O. et al., A Novel Heavy Domain Antibody Library with Functionally Optimized Complementarity Determining Regions, Plos One, 8(10), e76834, Oct. 2013, 15 pages.
Moutel, S. et al., A multi-Fc-species system for recombinant antibody production, BMC Biotechnol. 9, Article 14, 2009, 9 pages.
Provenzano, P. et al., Enzymatic targeting of the stroma ablates physical barriers to treatment of pancreatic ductal adenocarcinoma, Cancer Cell, 21(3): 418-29, 2012.
Salamon, J. et al., Antibody Directed against Human YKL-40 Increases Tumor Volume in a Human Melanoma Xenograft Model in Scid Mice, PLoS ONE, 9(4): e95822, 2014, 11 pages.
Schönfeld, K. et al., Activity of Indatuximab Ravtansine against Triple-Negative Breast Cancer in Preclinical Tumor Models, Pharm Res, 35, Article 118, 2018, 10 pages.
Shao, R. et al., Anti-YKL-40 antibody and ionizing irradiation synergistically inhibit tumor vascularization and malignancy in glioblastoma, Carcinogenesis, 35(2): 373-82, 2014.

* cited by examiner

*Primary Examiner* — Sharon X Wen
(74) *Attorney, Agent, or Firm* — Julie K. Staple; Dinsmore & Shohl LLP

(57) ABSTRACT

Provided herein are antibodies capable of binding to YKL-40. These YKL-40 antibodies are suitable for multiple purposes, for example for detection of YKL-40.

10 Claims, 1 Drawing Sheet
Specification includes a Sequence Listing.

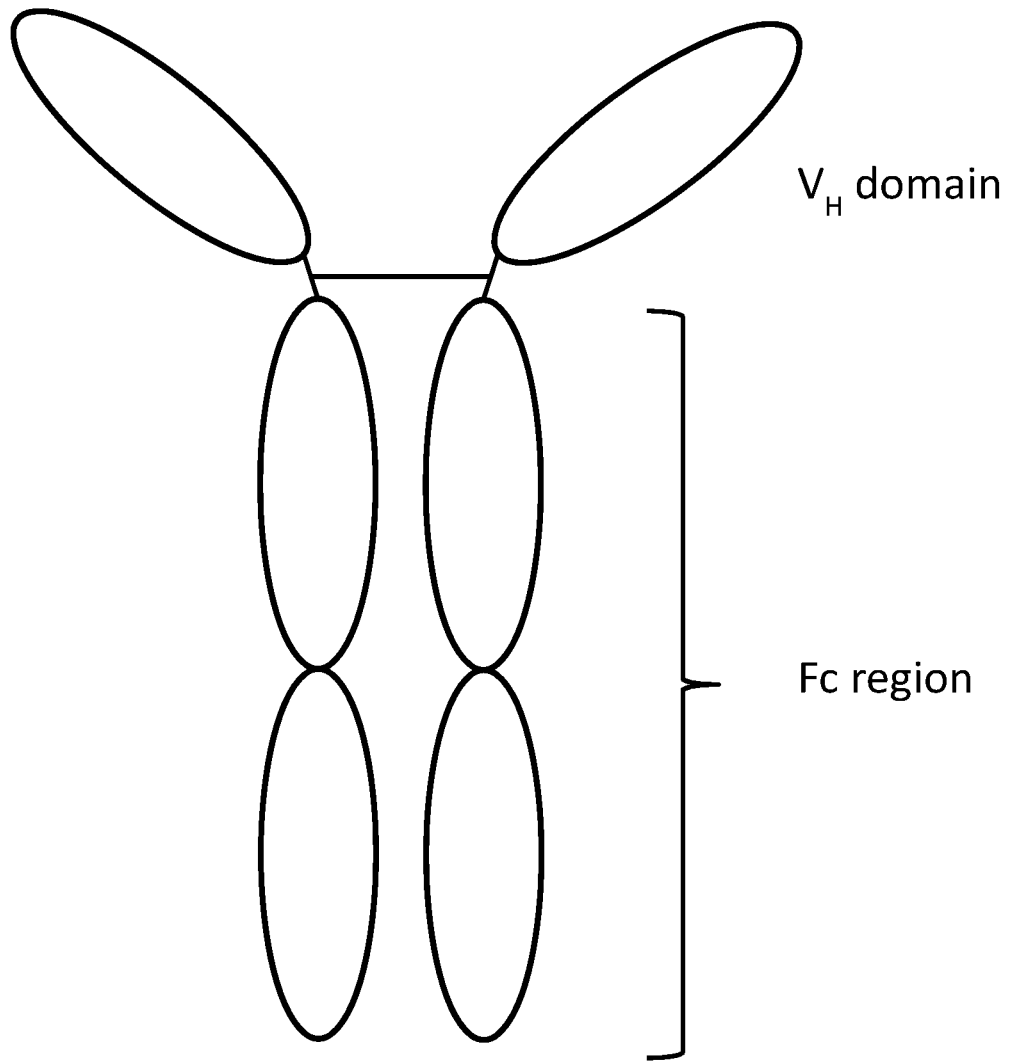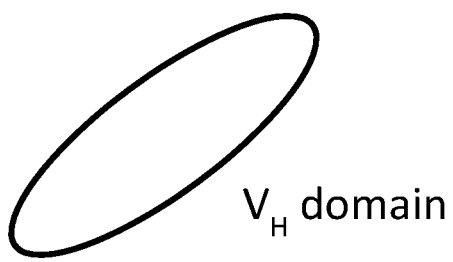

YKL-40 ANTIBODY

TECHNICAL FIELD

The present invention relates to YKL-40 antibodies capable of binding to YKL-40. These antibodies are useful for multiple purposes, for example for detection of YKL-40.

BACKGROUND

YKL-40 is a 40 kDa heparin- and chitin-binding glycoprotein also known as human cartilage glycoprotein 39 (HC gp-39), 38-kDa heparin-binding glycoprotein or chitinase-3-like protein 1 (CHI3L1). The abbreviation YKL-40 is based on the one letter code for the first three N-terminal amino acids, tyrosine (Y), lysine (K) and leucine (L) and the apparent molecular weight of YKL-40.

YKL-40 was first identified as a protein secreted in large amounts by a human osteosarcoma cell line MG63 in vitro. Later studies have found that YKL-40 is secreted in vitro by a variety of cells and seems especially involved in activation of the innate immune system and in cell processes in relation to extracellular matrix remodeling.

The crystallographic structure of human YKL-40 has been described and the protein contains two globular domains: a big core domain which consists of a $(\beta/\alpha)_8$ domain structure with a triose-phosphase isomerase (TIM) barrel fold and a small $\alpha/\beta$ domain, composed of five antiparallel $\beta$-strands and one $\alpha$-helix, inserted in the loop between strand $\beta7$ and helix $\alpha7$. This confers the active site of YKL-40 a groove-like character.

Besides binding to heparin and chitin, YKL-40 can also bind to hyaluronan. The folded protein contains two potential hyaluronan binding sites on the external face. Binding of short and long oligosaccharides to human YKL-40 are also possible.

YKL-40 possesses a number of biological activities. It has been shown that human YKL-40 can acts as a growth factor for cells of connective tissue, such as chondrocytes and synovial cells. YKL-40 also promotes the growths of fibroblasts in a fashion similar to insulin-like growth factor 1 (IGF-1). It has also been demonstrated that YKL-40 can act as a chemoattractant for endothelial cells and stimulates migration of these cells comparable to stimulation by basic fibroblast growth factor. YKL-40 is also found to modulate vascular endothelial cell morphology by promoting formation of branching tubules. A strong expression of YKL-40 mRNA in human liver has been shown to be associated with the presence of fibrosis. Immunohistochemical studies of liver biopsies have shown YKL-40 protein expression in areas of the liver with fibrosis, whereas no expression was observed in hepatocytes. Patients with non-malignant diseases characterized by inflammation and fibrosis such as active rheumatoid arthritis, severe bacteria infections, active inflammatory bowel disease, and liver fibrosis have elevated serum YKL-40.

YKL-40 is expressed and secreted by several types of human carcinomas. Furthermore, YKL-40 is found to be secreted in vitro by the osteoscarcoma cell line MG63, glioblastoma cells and myeloid leukemia cell lines. A number of studies have reported an elevated level of YKL-40 protein in serum of cancer patients.

Thus, YKL-40 activity is found to be associated with cell growth, survival, differentiation, apoptosis, angiogenesis, extracellular matrix remodeling, development of metastasis, development of liver or tissue fibrosis, development of rheumatoid arthritis and/or development of inflammation.

SUMMARY

There is an unmet need of additional YKL-40 antibodies, and particularly for human or humanised YKL-40 antibodies. The present invention provides antibodies, which are capable of binding to YKL-40. The inventors have demonstrated that the YKL-40 antibodies as described herein display good binding properties to YKL-40. Furthermore, the antibodies contains mainly human antibody sequences.

In one aspect, the present invention relates to an YKL-40 antibody comprising a variable region comprising a CDR1, CDR2 and CDR3, wherein CDR1 comprises or consists of an amino acid sequence of SEQ ID NO:20

CDR2 comprises or consists of an amino acid sequence of the general formula:

$$\text{SIX}_1\text{X}_2\text{X}_3\text{X}_4\text{GSTYYADSV} \quad \text{(SEQ ID NO: 55)}$$

wherein:
  $X_1$ is Q, S, N, D, G, E or Y;
  $X_2$ is S, G, N, A, D or Y;
  $X_3$ is S, E, N, Y, G, D or P;
  $X_4$ is D, G, S or N.

CDR3 comprises or consists of an amino acid sequence selected from the group consisting of SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54 and/or SEQ ID NO:57.

In one aspect, the present invention relates to an YKL-40 antibody comprising or consisting of a variable region comprises or consists of an amino acid sequence selected from the group consisting of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18 and SEQ ID NO:19.

DESCRIPTION OF DRAWINGS

FIG. 1. shows two common antibody formats. Different fragments from the immunoglobulin are often used in recombinant formats, especially the variable domains of the heavy chain $V_H$ have been used repeatedly. A) a variable domain of the heavy chain ($V_H$) linked to a constant region of the heavy chain (Fc region). B) a variable domain of the heavy chain ($V_H$).

DETAILED DESCRIPTION

Definitions

The term "antibody" as used herein refers to a polypeptide, which is capable of binding a specific antigen via an epitope on the antigen. An antibody comprises at least one antigen binding site, wherein said antigen binding site comprises 3 CDRs, such as a CRD1, CDR2 and CDR3. The antigen binding site may in particular be a variable region, such as a heavy chain or light chain variable region. Whereas most antibodies comprises a heavy chain comprising an antigen binding site and a light chain comprising another an antigen binding site, some antibodies are single-domain antibodies comprising only one antigen binding site. Single-domain antibodies consisting of heavy chains only are e.g. found in camelids. Typically, the antigen binding site of an antibody is positioned within an antibody variable region. Suitable variable regions include, but are not necessarily limited to Fv fragments, heavy chain variable regions and light chain variable regions. Variable regions may be connected and thus they may form or be part of e.g. single chain Fv (scFv) and disulphide-bonded Fv, Fab-like fragments (e.g. Fab fragments, Fab' fragments and F (ab) 2 fragments), and domain antibodies (dAbs, including single and dual formats [i.e. dAb-linker-dAb]). Variable regions may be linked to an Fc region. Thus, an antibody heavy chain usually consist of a heavy chain variable region and a heavy chain Fc region. Similarly, an antibody light chain usually consist of a light chain variable region and a light chain Fc region. Single-domain antibodies typically consists of variable region comprising 3 CDRs and a constant region of a heavy chain in one polypeptide. Various antibody chains may be linked to each other, e.g. by disulphide bonds. Thus, a heavy chain and a light chain may be linked to each other. Furthermore, a heavy chain and a light chain pair, may be linked to another (frequently identical) heavy chain/light chain pair. The heavy chain of a single domain antibody may also be linked to another (frequently identical) heavy chain, e.g. by disulphide bonds, thereby forming an antibody made up of two constant domains of the heavy chains and two variable domains of the heavy chain, wherein said Fc regions are joined by disulphide bonds (see FIG. 1).

The term "Fc region" is abbreviated form of "fragment crystallisable region". "Fc region" as used herein refers to the C-terminal constant region of an immune globulin heavy chain. The Fc region may be a "native" or "wild-type" sequence Fc region, or a variant Fc region. The Fc region may be any constant region of IgM, IgD, IgG IgA and IgE. A native Fc region is normally homodimeric and comprises two polypeptide chains. In respect of preparing YKL-40 antibodies a variable domain, such as $V_H$, may be linked to a "single-chain" Fc region (scFc region), which may later form a dimeric antibody comprising two $V_H$ domains and two scFc regions.

The term "naturally occurring antibody" refers to an antibody comprising two identical heavy chains and two identical light chains linked to another, wherein the heavy and light chains of the antibody have been made and paired by the immune system of a multi-cellular organism. Spleen, lymph nodes, bone marrow and serum are examples of tissues that produce natural antibodies. For example, the antibodies produced by the antibody producing cells isolated from a first animal immunized with an antigen are natural antibodies. Naturally occurring antibody are heterotetrameric glycoproteins capable of recognising and binding an antigen and comprising two identical heavy (H) chains and two identical light (L) chains inter-connected by disulfide bonds. Each heavy chain comprises a heavy chain variable region (abbreviated herein as $V_H$) and a heavy chain constant region (abbreviated herein as $C_H$). Each light chain comprises a light chain variable region (abbreviated herein as $V_L$) and a light chain constant region (abbreviated herein as $C_L$). The $V_H$ and $V_L$ regions can be further subdivided into regions of hypervariability, termed complementarity determining regions (CDRs), interspersed with regions that are more conserved, termed framework regions (FRs). Antibodies may comprise several identical heterotetramers.

The term "monoclonal antibody" as used herein refers to an antibody obtained from a population of substantially homogeneous antibodies, i.e., the individual antibodies making up the population are identical except for possible minor differences. Said minor differences may be the result of post-translational modification and/or degradation or they may be caused by naturally occurring mutations that may be present in minor amounts.

YKL-40 Antibody

The YKL-antibody of the present invention may be any YKL-40 antibody, wherein said YKL-40 antibody comprises a variable region as defined herein below in the section "Variable region". Thus, the present invention provides antibodies capable of binding to YKL-40, and preferably capable of binding human YKL-40. In particular, said antibodies are capable of binding to an amino acid sequence of SEQ ID NO:1.

YKL-40 is an extracellular matrix protein, specifically a secretory glycoprotein, which belongs to the mammalian chitinase like family. YKL-40 has been shown to bind collagen, heparin, hyaluronan and chitin. It is mainly produced by macrophages, neutrophils and cancer cells. YKL-40 plasma levels are increased in cancer patients compared to healthy subjects.

An antibody that is contemplated for use in the present invention can be in any of a variety of forms, including a whole immunoglobulin, an antibody fragment such as Fv, Fab, Fab' or $F(ab')_2$ fragments, a single chain antibody which comprises the variable regions of a heavy and a light chain linked together or single domain antibodies.

In a preferred embodiment, the antibody of the invention is a single domain antibody. Single domain antibodies usually comprises a variable region optionally linked to an Fc region. Thus, the antibody of the invention may consist of a variable region. Alternatively, the antibody may consist of a variable region linked to an Fc region. The variable region may for example consist of either of a $V_H$ domain or a $V_L$ domain, or another similar variable region. In particular, the single domain antibody may comprise a variable region and an Fc region derived from a human antibody, e.g. from a human heavy chain.

In one embodiment, the antibody comprises a variable region comprising a CRD1, CDR2 and CDR3 as defined herein below. The variable region may be selected from the group consisting of a $V_H$ domain, $V_L$ domain or scFv. It is preferred that the variable region comprises or consists of a $V_H$ domain.

In another embodiment, the variable region of said antibody is linked to an Fc region, optionally by a linker. Thus, the antibody according to the invention may comprise or consist of a $V_H$ domain linked to an Fc region, optionally via a linker. Hereby forming a single chain antibody which comprises the CDRs of a variable domain of the heavy chain and the constant region of the heavy chain in one polypeptide.

In yet another embodiment, the antibody may comprise or consist of two single domain antibodies. Thus, the antibody according to the invention may consist or comprise of two $V_H$ domains, wherein each $V_H$ domain is linked to an Fc region, wherein said Fc regions are linked to each other by bonds, such as by disulphide bonds.

The antibodies according to the present invention are in general monoclonal antibodies.

The antibody can be a multispecific antibody (e.g. bispecific antibody) formed from at least two different antibodies, and/or antibody fragments so long as they exhibit binding to YKL-40.

In one embodiment, the antibody is a chimeric antibody wherein the variable part is fused with an Fc region of a different species.

In one embodiment, the antibody is a human antibody or an antibody based on human scaffold. For example, the antibody may be a human single domain antibody. Human single domain antibodies may in particular comprise or consists of a human $V_H$ domain optionally linked to a human Fc region. The antibody may also be a single domain antibody based on human sequences, wherein diversity has been generated synthetically. The antibody may also be a humanised antibody comprising CDR regions (and possibly a few other residues) transferred from another species having the desired specificity, affinity, and capacity. Humanised antibodies may also comprise synthetic CDR regions, e.g. from a synthetic antibody library.

The generation of antibodies may be achieved by any standard methods in the art for producing antibodies.

For generation and/or selection of YKL-40 antibodies, YKL-40 protein or a fragment thereof is used. Preferably the method comprises use of a natural YKL-40 protein, such as a secreted and optionally purified YKL-40 protein. Alternatively, a recombinant YKL-40 protein or fragment thereof may also be employed. In particular, YKL-40 secreted from MG63 cells may be employed. Medium in which MG63 cells have been cultivated may be used in crude form or YKL-40 may be partly or fully purified from such medium. Recombinant antibodies may be isolated from libraries of genes encoding fragments of antibodies, e.g. using aforementioned YKL-40 protein or fragments thereof for selection. The fragments of antibodies can for example be any of the aforementioned antibody fragments, such as Fab, Fv fragments, single chain fragment of heavy and light chain variable domains or single domain antibodies, such as polypeptides comprising or consisting of $V_H$ or $V_L$ domains. The libraries of genes may be obtained from natural sources, as in the case of naïve or immunised libraries, or they may be created by synthetic means. Isolation of specific antibodies from the libraries can be mediated by panning of phage displayed antibody libraries on specific antigens or complex mixtures, such as described in Mandrup et al., 2013. Alternatively, methods such as yeast display, bacterial display, ribosome display, etc. can be applied in the selection of monoclonal recombinant antibodies.

The antibody may be a human single domain antibody or a single domain antibody based on human sequences, wherein diversity has been artificially generated. Several different libraries of useful human single domain antibodies are available. Thus, the antibody may be selected by screening any library of human single domain antibodies with YKL-40 protein or fragment(s) thereof. Such libraries include, but are not limited to human domain antibody libraries using the HEL4 scaffold, as well as such libraries, which have been counter-selected for aggregation, wherein the CDR regions of the resulting clones have been subcloned and used for generating a new library with diversity in all three CDR regions as described in Christ et al., 2007. Other useful libraries include Pansri et al., 2009, Rothe et al., 2008, Fellouse et al., 2007, Hust et al., 2004, Silacci et al., 2005 and Brockmann et al., 2011.

A preferred library to be used is the domain antibody library with constant CDR1 and restricted randomizations at 4 and 7 positions in the CDR2 and CDR3 described in Mandrup et al., 2013. This library is based on the aggregation resistant human HEL4 domain antibody scaffold with the inclusion of a hydrophilic mutation at position 29. The diversity of this library is designed to reflect the amino acid composition of CDR regions from known functional human antibody clones.

Once a variable domain capable of binding YKL-40 has been selected, said variable domain may be used as YKL-40 antibody per se, but it may also be fused to other domains, e.g. an Fc domain.

This may e.g. be achieved by using an expression vector allowing fusion of single chain Fv antibodies or single domains, such as single $V_H$ domains to Fc regions of immunoglobulins. This method is useful for the generation of multi-species antibodies and enables fusion of single chain Fv antibodies or single $V_H$ domains with human, mouse or rabbit Fc and can be applied to natural monoclonal antibodies cloned as single chain Fv antibodies. The expression vector can be for example a pFuse expression system, such as pFUSE-hFc1 or pFUSE-hFc1 as described by Moutel et al., 2009. Thus, an antibody comprising or consisting of a $V_H$ domain linked to an Fc region can be generated. Such antibodies can then dimerize and form an antibody of two $V_H$ domain which are each linked to an Fc region, wherein the two Fc regions are linked by disulphide bonds. Preferably, said Fc region is a human Fc region. Non-limiting examples of useful Fc regions include the Fc region of SEQ ID NO:58 or SEQ ID NO:59.

Variable Region

The antibody according to the present invention comprises a variable region. The variable region can be in any form, comprising a CDR1, CDR2 and CDR3. Thus, the variable region may be a single domains consisting of either $V_H$ or $V_L$ domains, scFv, Fab, Fab' or F(ab')2 fragments. It is preferred that the variable region is a $V_H$ domain, for example a human $V_H$ domain or a $V_H$ domain based on human sequences, such as a $V_H$ domain as described by Mandrup et al., 2013.

The variable domains are for binding and determine the specificity of each particular antibody for its particular antigen. However, the variable region is not normally evenly distributed thought the variable region of antibodies. It is concentrated in CDRs also known as hyper variable regions. The more highly conserved portions of variable domains are called the framework (FR). The variable domains of native heavy and light chains each comprise four FR regions connected by three CDRs. It is preferred that the FR regions are human FR regions, or at least highly identical to human FR regions.

In one embodiment, the YKL-40 antibody comprises a variable region comprising a CDR1 comprising or consisting of an amino acid sequence of SEQ ID NO:20. The antibody may comprise one or more CDR1s, for example one CDR1 or two CDR1.

In another embodiment, the YKL-40 antibody comprises a variable region comprising a CDR2 comprising or consisting of an amino acid sequence of the general formula $$SIX_1X_2X_3X_4GSTYYADSV \qquad (SEQ\ ID\ NO:\ 55)$$

wherein:
$X_1$ is Q, S, N, D, G, E or Y;
$X_2$ is S, G, N, A, D or Y;
$X_3$ is S, E, N, Y, G, D or P;
$X_4$ is D, G, S or N.

In another embodiment, the YKL-40 antibody comprises a variable region comprising a CDR2 comprising of an amino acid sequence selected from the group consisting of SEQ ID NO: SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53 and/or SEQ ID NO:56. The YKL-40 antibody may comprise one or more CDR2s, for example one CDR2 or two CDR2. Said CDR2 may be the same or different CDR2s.

In yet another embodiment, the YKL-40 antibody comprises a variable region comprising a CDR3 comprising of an amino acid sequence selected from the group consisting of SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54 and/or SEQ ID NO:57. The antibody may comprise one or more CDR3s, for example one CDR3 or two CDR3. Said CDR3 may be the same or different CDR3s.

In one embodiment, the YKL-40 antibody comprises a variable region comprising a CDR1, CDR2 and CDR3, wherein
CDR1 comprises or consists of an amino acid sequence of SEQ ID NO:20
CDR2 comprises or consists of an amino acid sequence of the general formula:

$$SIX_1X_2X_3X_4GSTYYADSV \quad (SEQ\ ID\ NO:\ 55)$$

wherein:
$X_1$ is Q, S, N, D, G, E or Y;
$X_2$ is S, G, N, A, D or Y;
$X_3$ is S, E, N, Y, G, D or P;
$X_4$ is D, G, S or N.
CDR3 comprises or consists of an amino acid sequence selected from the group consisting of SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52 SEQ ID NO:54 and/or 57.

In one embodiment, the YKL-40 antibody comprises a variable region comprising a CDR1 of SEQ ID NO:20, CDR2 of SEQ ID NO:21 and SEQ ID NO:22.

In one embodiment, the YKL-40 antibody comprises a variable region comprising a CDR1 of SEQ ID NO:20, CDR2 of SEQ ID NO:23 and SEQ ID NO:24.

In one embodiment, the YKL-40 antibody comprises a variable region comprising a CDR1 of SEQ ID NO:20, CDR2 of SEQ ID NO:25 and SEQ ID NO:26.

In one embodiment, the YKL-40 antibody comprises a variable region comprising a CDR1 of SEQ ID NO:20, CDR2 of SEQ ID NO:27 and SEQ ID NO:28.

In one embodiment, the YKL-40 antibody comprises a variable region comprising a CDR1 of SEQ ID NO:20, CDR2 of SEQ ID NO:29 and SEQ ID NO:30.

In one embodiment, the YKL-40 antibody comprises a variable region comprising a CDR1 of SEQ ID NO:20, CDR2 of SEQ ID NO:31 and SEQ ID NO:32.

In one embodiment, the YKL-40 antibody comprises a variable region comprising a CDR1 of SEQ ID NO:20, CDR2 of SEQ ID NO:33 and SEQ ID NO:34.

In one embodiment, the YKL-40 antibody comprises a variable region comprising a CDR1 of SEQ ID NO:20, CDR2 of SEQ ID NO:35 and SEQ ID NO:36.

In one embodiment, the YKL-40 antibody comprises a variable region comprising a CDR1 of SEQ ID NO:20, CDR2 of SEQ ID NO:37 and SEQ ID NO:38.

In one embodiment, the YKL-40 antibody comprises a variable region comprising a CDR1 of SEQ ID NO:20, CDR2 of SEQ ID NO:39 and SEQ ID NO:40.

In one embodiment, the YKL-40 antibody comprises a variable region comprising a CDR1 of SEQ ID NO:20, CDR2 of SEQ ID NO:41 and SEQ ID NO:42.

In one embodiment, the YKL-40 antibody comprises a variable region comprising a CDR1 of SEQ ID NO:20, CDR2 of SEQ ID NO:43 and SEQ ID NO:44.

In one embodiment, the YKL-40 antibody comprises a variable region comprising a CDR1 of SEQ ID NO:20, CDR2 of SEQ ID NO:45 and SEQ ID NO:46.

In one embodiment, the YKL-40 antibody comprises a variable region comprising a CDR1 of SEQ ID NO:20, CDR2 of SEQ ID NO:47 and SEQ ID NO:48.

In one embodiment, the YKL-40 antibody comprises a variable region comprising a CDR1 of SEQ ID NO:20, CDR2 of SEQ ID NO:49 and SEQ ID NO:50.

In one embodiment, the YKL-40 antibody comprises a variable region comprising a CDR1 of SEQ ID NO:20, CDR2 of SEQ ID NO:51 and SEQ ID NO:52.

In one embodiment, the YKL-40 antibody comprises a variable region comprising a CDR1 of SEQ ID NO:20, CDR2 of SEQ ID NO:53 and SEQ ID NO:54.

In one embodiment, the YKL-40 antibody comprises a variable region comprising a CDR1 of SEQ ID NO:20, CDR2 of SEQ ID NO:56 and SEQ ID NO:57.

In one embodiment, the YLK-40 antibody comprises or even consists of a variable region, wherein said variable region comprises or consists of an amino acid sequence selected from the group consisting of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18 and SEQ ID NO:19.

In one embodiment, the antibody binds to YKL-40, wherein binding to YKL-40 inhibits or prevents binding of YKL-40 to another molecule. Binding of the antibody to YKL-40 can result in activation, stimulation or inhibition of YKL-40. Thus, binding of the antibody to YKL-40 may results in activation, stimulation or inhibition of YKL-40.

In one embodiment the antibody is an inhibitor of YKL-40. Thus, the YKL-40 antibody may results in inhibition of at least one function of YKL-40.

Fc Region

The antibody according to the present invention comprises a variable region, which may be linked to any Fc region.

Traditionally, antibodies have been grouped based on the constant domain of their heavy chains, i.e. Fc region, into five classes IgM, IgD, IgG IgA and IgE. Which can be further divided into subclasses (isotypes), e.g. IgG-1, IgG-2, IgG-3 and IgG-4; IgA-1 and IgA-2.

In some embodiments, the antibody according to the present invention comprises a variable region which may be linked to any constant region of another antibody. The constant region may be identical to a "native" or "wild-type" Fc region, or a variant Fc region with at least one alteration of an amino acid.

In one embodiment, the Fc region has the amino acid sequence of a human IgG Fc region or a human IgG2 Fc region. A suitable Fc region is described in Moutel et al., 2009.

Items

The invention may further be defined by the following items:

1. A YKL-40 antibody comprising a variable region comprising a CDR1, CDR2 and CDR3, wherein
   CDR1 comprises or consists of an amino acid sequence of SEQ ID NO:20
   CDR2 comprises or consists of an amino acid sequence of the general formula:

SIX$_1$X$_2$X$_3$X$_4$GSTYYADSV  (SEQ ID NO: 55)

wherein:
   X$_1$ is Q, S, N, D, G, E or Y;
   X$_2$ is S, G, N, A, D or Y;
   X$_3$ is S, E, N, Y, G, D or P;
   X$_4$ is D, G, S or N.
   CDR3 comprises or consists of an amino acid sequence selected from the group consisting of SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54 and/or SEQ ID NO:57.
2. The YKL-40 antibody according to item 1, wherein said variable region comprises or consists of a V$_H$ domain.
3. The YKL-40 antibody according to any one of the preceding items, wherein said variable region is linked to an Fc region, optionally via a linker.
4. The YKL-40 antibody according to any one of the preceding items, wherein the antibody consists of a variable region linked to an Fc region.
5. The YKL-40 antibody according to any one of the preceding items, wherein said YKL-40 antibody comprises or consists of two variable regions, wherein each variable region is linked to an Fc region, optionally by a linker, wherein said Fc regions are linked to each other.
6. The YKL-40 antibody according to any one of the preceding items, wherein said Fc regions are linked together by disulfide bonds.
7. The YKL-40 antibody according to any one of the preceding items, wherein the CDR2 comprises an amino acid sequence selected from the group consisting of SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53 and/or SEQ ID NO:56.
8. The YKL-40 antibody according to any one of the preceding items, wherein the variable region comprises a CDR1 of SEQ ID NO:20, CDR2 of SEQ ID NO:21 and SEQ ID NO:22.
9. The YKL-40 antibody according to any one of the preceding items, wherein the variable region comprises a CDR1 of SEQ ID NO:20, CDR2 of SEQ ID NO:23 and SEQ ID NO:24.
10. The YKL-40 antibody according to any one of the preceding items, wherein the variable region comprises a CDR1 of SEQ ID NO:20, CDR2 of SEQ ID NO:25 and SEQ ID NO:26.
11. The YKL-40 antibody according to any one of the preceding items, wherein the variable region comprises a CDR1 of SEQ ID NO:20, CDR2 of SEQ ID NO:27 and SEQ ID NO:28.
12. The YKL-40 antibody according to any one of the preceding items, wherein the variable region comprises a CDR1 of SEQ ID NO:20, CDR2 of SEQ ID NO:29 and SEQ ID NO:30.
13. The YKL-40 antibody according to any one of the preceding items, wherein the variable region comprises a CDR1 of SEQ ID NO:20, CDR2 of SEQ ID NO:31 and SEQ ID NO:32.
14. The YKL-40 antibody according to any one of the preceding items, wherein the variable region comprises a CDR1 of SEQ ID NO:20, CDR2 of SEQ ID NO:33 and SEQ ID NO:34.
15. The YKL-40 antibody according to any one of the preceding items, wherein the variable region comprises a CDR1 of SEQ ID NO:20, CDR2 of SEQ ID NO:35 and SEQ ID NO:36.
16. The YKL-40 antibody according to any one of the preceding items, wherein the variable region comprises a CDR1 of SEQ ID NO:20, CDR2 of SEQ ID NO:37 and SEQ ID NO:38.
17. The YKL-40 antibody according to any one of the preceding items, wherein the variable region comprises a CDR1 of SEQ ID NO:20, CDR2 of SEQ ID NO:39 and SEQ ID NO:40.
18. The YKL-40 antibody according to any one of the preceding items, wherein the variable region comprises a CDR1 of SEQ ID NO:20, CDR2 of SEQ ID NO:41 and SEQ ID NO:42.
19. The YKL-40 antibody according to any one of the preceding items, wherein the variable region comprises a CDR1 of SEQ ID NO:20, CDR2 of SEQ ID NO:43 and SEQ ID NO:44.
20. The YKL-40 antibody according to any one of the preceding items, wherein the variable region comprises a CDR1 of SEQ ID NO:20, CDR2 of SEQ ID NO:45 and SEQ ID NO:46.
21. The YKL-40 antibody according to any one of the preceding items, wherein the variable region comprises a CDR1 of SEQ ID NO:20, CDR2 of SEQ ID NO:47 and SEQ ID NO:48.
22. The YKL-40 antibody according to any one of the preceding items, wherein the variable region comprises a CDR1 of SEQ ID NO:20, CDR2 of SEQ ID NO:49 and SEQ ID NO:50.
23. The YKL-40 antibody according to any one of the preceding items, wherein the variable region comprises a CDR1 of SEQ ID NO:20, CDR2 of SEQ ID NO:51 and SEQ ID NO:52.
24. The YKL-40 antibody according to any one of the preceding items, wherein the variable region comprises a CDR1 of SEQ ID NO:20, CDR2 of SEQ ID NO:53 and SEQ ID NO:54.
25. The YKL-40 antibody according to any one of the preceding items, wherein the variable region comprises a CDR1 of SEQ ID NO:20, CDR2 of SEQ ID NO:56 and SEQ ID NO:57.
26. The YLK-40 antibody according to any one of the preceding items, wherein said variable region comprises or consists of an amino acid sequence selected from the group consisting of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18 and SEQ ID NO:19.

27. The YLK-40 antibody according to any one of the preceding items, wherein said antibody comprises or consists of a variable region consisting of an amino acid sequence selected from the group consisting of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18 and SEQ ID NO:19.

28. The YLK-40 antibody according to any one of the preceding items, wherein the antibody consists of a variable region consisting of an amino acid sequence selected from the group consisting of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18 and SEQ ID NO:19. linked to an Fc region.

29. The YLK-40 antibody according to item 27, wherein said antibody forms dimers.

30. The YKL-40 antibody according to any one of the preceding items, wherein the antibody comprises an Fc region, wherein the Fc region is a human Fc region.

31. The YKL-40 antibody according to any one of the preceding items, wherein the antibody comprises an Fc region comprising or consisting of SEQ ID NO: 58 or SEQ ID NO:59.

Sequences

```
SEQ ID NO: 1. Human YKL-40 also known as
Chitinase-3-like protein 1 (CHI3L1)
MGVKASQTGFVVLVLLQCCSAYKLVCYYTSWSQYREGDGSCFPDALDRFL
CTHIIYSFANISNDHIDTWEWNDVTLYGMLNTLKNRNPNLKTLLSVGGWN
FGSQRFSKIASNTQSRRTFIKSVPPFLRTHGFDGLDLAWLYPGRRDKQHF
TTLIKEMKAEFIKEAQPGKKQLLLSAALSAGKVTIDSSYDIAKISQHLDF
ISIMTYDFHGAWRGTTGHHSPLFRGQEDASPDRFSNTDYAVGYMLRLGAP
ASKLVMGIPTFGRSFTLASSETGVGAPISGPGIPGRFTKEAGTLAYYEIC
DPLRGATVHRILGQQVPYATKGNQWVGYDDQESVKSKVQYLKDRQLAGAM
VWALDLDDFQGSFCGQDLRFPLTNAIKDALAAT SEQ ID NO: 2. 4A2 predator
LLLLAAQPAMAEVQLLESGGGLVQPGGSLRLSCAASGFRDSDEDMGWVRQ
APGKGLEWVSSISTSDGSTYYADSVKGRFTISRDNSKNTLYLQMNSLRAE
DTAVYYCASQYDTGYSFDYWGQGTLVTVSSAAAEQKLISEEDLNGAATVE
SCLAKPHTENSFTNV SEQ ID NO: 3. 4G1 predator
LLLLAAQPAMAEVQLLESGGGLVQPGGSLRLSCAASGFRDSDEDMGWVRQ
APGKGLEWVSSIGDESGSTYYADSVKGRFTISRDNSKNTLYLQNSLRAED
TAVYYCASTSDSYWSFDYWGQGTLVTVSSAAAEQKLISEEDLNGAATVES
CLAKPHTENSFTNV SEQ ID NO: 4. 4H3 predator
LLLAAQPAMAEVQLLESGGGLVQPGGSLRLSCAASGFRDSDEDMGWVRQA
PGKGLEWVSSINAPDGSTYYADSVKGRFTISRDNSKNTLYLQMNSLRAED
TAVYYCASQWDDGYAFDYWGQGTLVTVSSAAAEQKLISEEDLNGAATVES
CLAKPHTENSFTNVW SEQ ID NO: 5. 4D6 predator
LLLLAAQPAMAEVQLLESGGGLVQPGGSLRLSCAASGFRDSDEDMGVVVR
QAPGKGLEWVSSISGSDGSTYYADSVKGRFTISRDNSKNTLYLQMNSLRA
EDTAVYYCASTDYLRSSFDYWGQGTLVTVSSAAAEQKLISEEDLNGAATV
ESCLAKPHTENSFTNV SEQ ID NO: 6. 4B6 predator
LLLLAAQPAMAEVQLLESGGGLVQPGGSLRLSCAASGFRDSDEDMGWVRQ
APGKGLEWVSSINNSGGSTYYADSVKGRFTISRDNSKNTLYLQMNSLRAE
DTAVYYCASTYDWNYSFDYWGQGTLVTVSSAAAEQKLISEEDLNGAATVE
SCLAKPHTENSFTNV SEQ ID NO: 7. 4A12 predator
LLLLAAQPAMAEVQLLESGGGLVQPGGSLRLSCAASGFRDSDEDMGWVRQ
APGKGLEWVSSISAESGSTYYADSVKGRFTISRDNSKNTLYLQMNSLRAE
DTAVYYCASQYGAYHDFDYWGQGTLVTVSSAAAEQKLISEEDLNGAATVE
SCLAKPHTENSFTNV SEQ ID NO: 8. 1X2 predator
LLLLAAQPAMAEVQLLESGGGLVQPGGSLRLSCAASGFRDSDEDMGWVRQ
APGKGLEWVSSINYNSGSTYYADSVKGRFTISRDNSKNTLYLQMNSLRAE
DTAVYYCASTPNLNSSFDYWGQGTLVTVSSAAAEQKLISEEDLNGAATVE
SCLAKPHTENSFTNV SEQ ID NO: 9. 2F6 predator
LLLLAAQPAMAEVQLLESGGGLVQPGGSLRLSCAASGFRDSDEDMGWVRQ
APGKGLEWVSSISDEDGSTYYADSVKGRFTISRDNSKNTLYLQMNSLRAE
DTAVYYCASSGDWWYGFDYWGQGTLVTVSSAAAEQKLISEEDLNGAATVE
SCLAKPHTENSFTNV SEQ ID NO: 10. 2D7 predator
LLLLAAQPAMAEVQLLESGGGLVQPGGSLRLSCAASGFRDSDEDMGWVRQ
APGKGLEWVSSISGESGSTYYADSVKGRFTISRDNSKNTLYLQMNSLRAE
DTAVYYCASVDPLDTYFDYWGQGTLVTVSSAAAEQKLISEEDLNGAATVE
SCLAKPHTENSFTNV SEQ ID NO: 11. 4F3 predator
LLLLAAQPAMAEVQLLESGGGLVQPGGSLRLSCAASGFRDSDEDMGWVRQ
APGKGLEWVSSIQSSDGSTYYADSVKGRFTISRDNSKNTLYLQMNSLRAE
DTAVYYCASSSQNGYVFDYWGQGTLVTVSSAAAEQKLISEEDLNGAATVE
SCLAKPHTENSFTNV SEQ ID NO: 12. 2H12 predator
LLLLAAQPAMAEVQLLESGGGLVQPGGSLRLSCAASGFRDSDEDMGWVRQ
APGKGLEWVSSINNESGSTYYADSVKGRFTISRDNSKNTLYLQMNSLRAE
DTAVYYCASTSYYGFDFDYWGQGTLVTVSSAAAEQKLISEEDLNGAATVE
SCLAKPHTENSFTNV SEQ ID NO: 13. 2B8 predator
LLLLAAQPAMAEVQLLESGGGLVQPGGSLRLSCAASGFRDSDEDMGWVRQ
APGKGLEWVSSIYAPNGSTYYADSVKGRFTISRDNSKNTLYLQMNSLRAE
DTAVYYCASNTYDAFDYWGQGTLVTVSSAAAEQKLISEEDLNGAATVESC
LAKPHTENSFTNVWK SEQ ID NO: 14. 4D9 predator
LLLLAAQPAMAEVQLLESGGGLVQPGGSLRLSCAASGFRDSDEDMGWVRQ
APGKGLEWVSSIASDSGSTYYADSVKGRFTISRDNSKNTLYLQMNSLRAE
DTAVYYCASSGYAGTVFDYWGQGTLVTVSSAAAEQKLISEEDLNGAATVE
SCLAKPHTENSFTNVWKDDKTLDRYANYEGCLWNATGVVVCT SEQ ID NO: 15. 2F3 predator
LLLLAAQPAMAEVQLLESGGGLVQPGGSLRLSCAASGFRDSDEDMGWVRQ
APGKGLEWVSSIGAGSGSTYYADSVKGRFTISRDNSKNTLYLQMNSLRAE
DTAVYYCASSTDARWQFDYWGQGTLVTVSSAAAEQKLISEEDLNGAATVE
SCLAKPHTENSFTNV SEQ ID NO: 16. 3F12 predator
LLLLAAQPAMAEVQLLESGGGLVQPGGSLRLSCAASGFRDSDEDMGWVRQ
APGKGLEWVSSINANDGSTYYADSVKGRFTISRDNSKNTLYLQMNSLRAE
DTAVYYCASQYDDEFAFDYWGQGTLVTVSSAAAEQKLISEEDLNGAATVE
SCLAKPHTENSFTNV SEQ ID NO: 17. 4D5 predator
LLLLAAQPAMAEVQLLESGGGLVQPGGSLRLSCAASGFRDSDEDMGWVRQ
APGKGLEWVSSIGNYNGSTYYADSVKGRFTISRDNSKNTLYLQMNSLRAE
DTAVYYCASVSDSGFSFDYWGQGTLVTVSSAAAEQKLISEEDLNGAATVE
SCLAKPHTENSFTNV
```

SEQ ID NO: 18. 4E10 predator
LLLLAAQPAMAEVQLLESGGGLVQPGGSLRLSCAASGFRDSDEDMGWVRQ
APGKGLEWVSSIYGPSGSTYYADSVKGRFTISRDNSKNTLYLQMNSLRAE
DTAVYYCASSDWDGYSFDYWGQGTLVTVSSAAAEQKLISEEDLNGAATVE
SCLAKPHTENSFTNV SEQ ID NO: 19. 2D3 predator
LLLLAAQPAMAEVQLLESGGGLVQPGGSLRLSCAASGFRDSDEDMGWVRQ
APGKGLEWVSSIDAEDGSTYYADSVKGRFTISRDNSKNTLYLQMNSLRAE
DTAVYYCASQDGAYYTFDYWGQGTLVTVSSAAAEQKLISEEDLNGAATVE
SCLAKPHTENSFTNV

SEQ ID NO: 20. CDR1
FRDSDEDMG

SEQ ID NO: 21. 4G1 CDR2
SIGDESGSTYYADSV

SEQ ID NO: 22. 4G1 CDR3
TSDSYWSFDY

SEQ ID NO: 23. 4H3 CDR2
SINAPDGSTYYADSV

SEQ ID NO: 24. 4H3 CDR3
QWDDGYAFDY

SEQ ID NO: 25. 4D6 CDR2
SISGSDGSTYYADSV

SEQ ID NO: 26. 4D6 CDR3
TDYLRSSFDY

SEQ ID NO: 27. 4B6 CDR2
SINNSGGSTYYADSV

SEQ ID NO: 28. 4B6 CDR3
TYDWNYSFDY

SEQ ID NO: 29. 4A12 CDR2
SISAESGSTYYADSV

SEQ ID NO: 30. 4A12 CDR3
QYGAYHDFDY

SEQ ID NO: 31. 1X2 CDR2
SINYNSGSTYYADSV

SEQ ID NO: 32. 1X2 CDR3
TPNLNSSFDY

SEQ ID NO: 33. 2F6 CDR2
SISDEDGSTYYADSV

SEQ ID NO: 34. 2F6 CDR3
SGDWWYGFDY

SEQ ID NO: 35. 2D7 CDR2
SISGESGSTYYADSV

SEQ ID NO: 36. 2D7 CDR3
VDPLDTYFDY

SEQ ID NO: 37. 4F3 CDR2
SIQSSDGSTYYADSV

SEQ ID NO: 38. 4F3 CDR3
SSQNGYVFDY

SEQ ID NO: 39. 2H12 CDR2
SINNESGSTYYADSV

SEQ ID NO: 40. 2H12 CDR3
TSYYGFDFDY

SEQ ID NO: 41. 2B8 CDR2
SIYAPNGSTYYADSV

SEQ ID NO: 42. 2B8 CDR3
NTYDAFDY

SEQ ID NO: 43. 4D9 CDR2
SIASDSGSTYYADSV

SEQ ID NO: 44. 4D9 CDR3
SGYAGTVFDY

SEQ ID NO: 45. 2F3 CDR2
SIGAGSGSTYYADSV

SEQ ID NO: 46. 2F3 CDR3
STDARWQFDY

SEQ ID NO: 47. 3F12 CDR2
SINANDGSTYYADSV

SEQ ID NO: 48. 3F12 CDR3
QYDDEFAFDY

SEQ ID NO: 49. 4D5 CDR2
SIGNYNGSTYYADSV

SEQ ID NO: 50. 4D5 CDR3
VSDSGFSFDY

SEQ ID NO: 51. 4E10 CDR2
SIYGPSGSTYYADSV

SEQ ID NO: 52. E10 CDR3
SDWDGYSFDY

SEQ ID NO: 53. 2D3 CDR2
SIDAEDGSTYYADSV

SEQ ID NO: 54. 2D3 CDR3
QDGAYYTFDY

SEQ ID NO: 55. CDR2 general formula
SIX$_1$X$_2$X$_3$X$_4$GSTYYADSV

SEQ ID NO: 56. 4A2 CDR2
SISTSDGSTYY

SEQ ID NO: 57. 4A2 CDR3
QYDTGYSFDY

SEQ ID NO: 58
Amino acid sequence of hFc1
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSREEMTKNQVSLTCLVK

GFYPSDIAVEWESNGQPENNYKTTPPVLDSDGSFFLYSKLTVDKSRWQQG

NVFSCSVMHEALHNHYTQKSLSLSPGK

SEQ ID NO: 59
Amino acid sequence of hFc2
VECPPCPAPPVAGPSVFLFPPKPKDTLMISRTPEVTCVVVDVSHEDPEVQ

FNWYVDGMEVHNAKTKPREEQFNSTFRVVSVLTVVHQDWLNGKEYKCKVS

NKGLPAPIEKTISKTKGQPREPQVYTLPPSREEMTKNQVSLTCLVKGFYP

SDIAVEWESNGQPENNYKTTPPMLDSDGSFFLYSKLTVDKSRWQQGNVFS

CSVMHEALHNHYTQKSLSLSPGK

EXAMPLES

Example 1 Selection of Phage Antibodies Recognizing YKL-40

YKL-40 Protein
YKL-40 protein was obtained from the supernatant of MG63. MG63 production flasks were seeded at 1.8×10$^4$ cells/cm$^2$ in RPMI-40 (Irvine Scientific) plus newborn calf serum, 100 mL/L (Irvine Scientific), 0.1 mol/L HEPES, and 50 mg/L vitamin C (complete medium). Flasks were incubated at 37° C. with humidity and CO2-enriched (100 mL/L) atmosphere for 6-8 days, replacing spent medium with fresh every 2-3 days. The cultures were then switched to serum-free medium (complete medium minus the newborn calf serum). The supernatants were harvested and the media replaced every 1-3 days for 30 days. YKL-40 protein was purified from the supernatants by concentrating glass-fiber-filtered material 20-fold with a 30-kDa screen channel cassette with tangential flow (Filtron) and then affinity-purifying over a heparin-Sepharose CL-6B column (Pharmacia Biotech) equilibrated with a solution of 10 mmol/L sodium phosphate and 50 mmol/L sodium chloride, pH 7.5. Bound material was eluted with a sodium chloride gradient (from 50 mmol/L to 2 mol/L) in 10 mmol/L sodium phosphate, pH 7.5, and 4-mL fractions were collected and pooled according to: absorbance at 280 nm, YKL-40 protein concentration by immunoassay, and purity by sodium dodecyl sulfate-polyacrylamide gel electrophoresis.

Phage Rescue

Selection of phage antibodies recognizing YKL-40 were performed using a predator antibody library, which is a single scaffold domain library with variation in CDR2 and CDR3. (Mandrup, Friis et al. 2013) against the purified YKL-40 protein. Thus, the antibodies of this library are single domain antibodies.

First a plastic immunotube was coated overnight with YKL-40 at 4° C., so the antigen could be partially absorbed by the plastic and anchored to the inner surface of the tube.

The day after the tube was washed 5 times with PBS and incubate with 2% BSA in PBS for 2 hours at room temperature (RT). After another round of washing, 100 µl of the phage antibody library pREDATOR was added in 4 ml of 2% BSA in PBS. The phage antibody library was incubated for 60 min at RT rotating using an under- and over turntable and then further 60 min at RT standing on the bench. Unbound phages were washed away with 10 washes in PBS containing 0.1% Tween 20 and 10 washes with PBS.

Bound phages were eluted by adding 500 µl of trypsin-PBS (50 µl of 10 mg/ml trypsin stock solution added to 450 µl PBS) and incubating on rotating for 10 min at RT.

The eluent was then incubate with 10 ml of TG1 (*E. coli*) in exponential growth (at an OD 600 of 0.4) for 30 min at 37° C. The bacteria were then plated on TYE plates containing 100 µg/ml ampicillin and 1% glucose and grown overnight at 30° C. The following day individual colonies from the plates were picked up with a toothpick and put in a well of a 96 cell-well plate containing 2×TY medium with 100 µg/ml ampicillin and 1% glucose and grown on a shaker overnight at 37° C. The day after a transfer device was used to transfer a small inoculum from this plate (the master plate) to a second 96 cell-well plate containing the same medium. Bacteria was grown shaking at 37° C. for 2 hours, new medium containing Helper phage, KM13 was added. The plate were incubated for 1 hour at 37° C. to let the Helper infect the cell, after this media was changed to 2×TY medium containing 100 µg/ml Ampicillin and 50 µg/ml of Kanamycin, finally the bacteria were incubate at 30° C., on shaking, overnight. The supernatant was used for ELISA.

Selection and Amplification Rounds

One round of selection was performed before screening the individual clones (to preserve diversity of binders regardless of affinity). The selection was run on all phage antibodies.

Screening Rounds

Preliminary Screening

After selection the eluted phages were infected in the *E. coli* TG-1 and spread on Amp selective agar plates. Around 500 colonies were obtained. These were inoculated in 100 µl 2×TY in 96 well plates. Phage antibodies were produced from the plates using the helper phage KM13 according to standard procedures.

Example of Preliminary Screening

After coating with used (MG63 conditioned) or fresh media, the ELISA plate were blocked with 2% skimmed milk powder in PBS. After blocking 50 µl of the phage supernatant were added to each well and incubated. The plates were washed and incubated with 1:5000 diluted anti-M13 antibody (HRP conjugated). After washing the ELISA plate were developed using TMB and the plate read in an ELISA reader.

76 clones were selected as positive if they had a significant higher signal on the conditioned plate compared to fresh media plate. Clones were named according to plate and position on plate e.g. 3B2, which would be the clone on the third plate in row B column 2 (see table 1 below).

TABLE 1

| Temperat | 1 | 2 | 3 | 4 | 5 | 6 | 7 | 8 | 9 | 10 | 11 | 12 |
|---|---|---|---|---|---|---|---|---|---|---|---|---|
| Plate 3 Used Media | | | | | | | | | | | | |
| A | 0.056 | 0.082 | 0.045 | 0.048 | 0.133 | 0.051 | 0.048 | 0.089 | 0.292 | 0.304 | 0.217 | 0.065 |
| B | 0.051 | | 0.044 | 0.518 | 0.16 | 0.093 | 0.405 | 0.048 | 0.047 | 0.047 | 0.044 | 0.081 |
| C | 0.077 | 0.043 | 0.043 | 0.205 | 0.062 | 0.043 | 0.046 | 0.054 | 0.259 | 0.044 | 0.054 | 0.074 |
| D | 0.043 | 0.055 | 0.406 | 0.046 | 0.051 | 0.251 | 0.044 | 0.043 | 0.045 | 0.431 | 0.049 | 0.049 |
| E | 0.046 | 0.044 | 0.044 | 0.184 | 0.049 | 0.044 | 0.049 | 0.043 | 0.051 | 0.105 | 0.042 | 0.055 |
| F | 0.071 | 0.046 | 0.431 | 0.045 | 0.443 | 0.263 | 0.279 | 0.693 | 0.101 | 0.046 | 0.088 | |
| G | 0.053 | 0.051 | 0.062 | 0.062 | 0.043 | 0.043 | 0.044 | 0.044 | 0.044 | 0.055 | 0.047 | 0.107 |
| H | | 0.059 | 0.052 | 0.077 | 0.046 | 0.07 | 0.123 | 0.082 | 0.051 | 0.058 | 0.062 | 0.058 |
| Plate 3 control Fresh Media | | | | | | | | | | | | |
| A | 0.044 | 0.061 | 0.058 | 0.053 | 0.063 | 0.046 | 0.058 | 0.063 | 0.042 | 0.046 | 0.052 | 0.049 |
| B | 0.056 | 0.047 | 0.047 | 0.044 | 0.044 | 0.045 | 0.043 | 0.043 | 0.043 | 0.042 | 0.042 | 0.043 |
| C | 0.066 | 0.044 | 0.043 | 0.046 | 0.044 | 0.043 | 0.043 | 0.043 | 0.043 | 0.042 | 0.042 | 0.045 |
| D | 0.056 | 0.044 | 0.044 | 0.043 | 0.043 | 0.044 | 0.043 | 0.043 | 0.043 | 0.043 | 0.043 | 0.043 |
| E | 0.043 | 0.043 | 0.048 | 0.045 | 0.042 | 0.042 | 0.042 | 0.042 | 0.044 | 0.042 | 0.042 | 0.037 |
| F | 0.044 | 0.054 | 0.048 | 0.047 | 0.044 | 0.044 | 0.047 | 0.045 | 0.046 | 0.046 | 0.044 | 0.044 |
| G | 0.046 | 0.043 | 0.046 | 0.043 | 0.044 | 0.041 | 0.043 | 0.041 | 0.043 | 0.042 | 0.042 | 0.042 |
| H | 0.048 | 0.05 | 0.047 | 0.044 | 0.046 | 0.047 | 0.047 | 0.046 | 0.048 | 0.046 | 0.053 | 0.046 |

Dilution Series of the PEG Precipitated Phages

Selected clones which were judged potential positive in the preliminary screening were grown in 50 ml culture and rescued using the KM13 helper phage. After overnight growth the supernatant were PEG precipitated according to standard procedures, and the pellet resuspended in 1 ml PBS. As phage antibody concentration is highly enriched by growing in 50 ml baffled flasks, the phage antibody concentration after PEG precipitation is 100-1000 more concentrated compared to the initial screen.

The PEG precipitated phage were used in validating ELISA, were a dilution series of the PEG precipitated phage were applied to ELISA plates coated with MG63 conditioned media or Fresh media. ELISA were performed as above.

The results of the dilution series in shown in Table 2 below. "Used" as used in Table 2 refers to MG63 conditioned media containing YKL-40. MG63 cells produces YKL-40 and thus medium in which MG63 cells have been grown (MG63 conditioned media) contains YKL-40. "Fresh" as used in Table 2 refers to fresh media which has not been in contact with YKL-40 producing cells (MG63) and thus does not contain YKL-40. Row 1-12 represents a series of dilution. Row 1 represents 100 μl antibody concentrate from 50 ml baffled flasks. Row 2 is a 5× dilution of the concentrate from row 1. Row 3 is a 5× dilution from of the dilution from Row 2 etc.

TABLE 2

|  |  | Temperature | 1 | 2 | 3 | 4 | 5 | 6 | 7 | 8 | 9 | 10 | 11 | 12 |
|---|---|---|---|---|---|---|---|---|---|---|---|---|---|---|
| Used Plate 1 | 4C2 | 21.00 | 1.784 | 1.8 | 1.247 | 0.247 | 0.155 | 0.079 | 0.077 | 0.087 | 0.083 | 0.067 | 0.072 | 0.049 |
|  | 2F11 |  | 1.108 | 1.713 | 0.892 | 0.329 | 0.168 | 0.129 | 0.077 | 0.091 | 0.087 | 0.1 | 0.094 | 0.053 |
|  | 2A12 |  | 1.149 | 1.665 | 0.825 | 0.374 | 0.166 | 0.154 | 0.123 | 0.126 | 0.116 | 0.088 | 0.089 | 0.059 |
|  | 3F8 |  | 0.186 | 0.172 | 0.108 | 0.127 | 0.098 | 0.173 | 0.135 | 0.128 | 0.136 | 0.126 | 0.114 | 0.065 |
|  | 3C9 |  | 1.016 | 0.689 | 0.211 | 0.124 | 0.085 | 0.122 | 0.108 | 0.11 | 0.143 | 0.096 | 0.075 | 0.049 |
|  | 3F9 |  | 0.682 | 0.193 | 0.22 | 0.133 | 0.123 | 0.093 | 0.116 | 0.122 | 0.132 | 0.13 | 0.081 | 0.064 |
|  | 3A9 |  | 1.257 | 1.797 | 1.475 | 0.576 | 0.213 | 0.185 | 0.122 | 0.135 | 0.133 | 0.073 | 0.151 | 0.046 |
|  | 3B7 |  | 1.389 | 3.148 | 2.859 | 1.636 | 0.368 | 0.132 | 0.148 | 0.094 | 0.086 | 0.076 | 0.057 | 0.06 |
| Fresh Plate 1 | 4C2 | 21.10 | 0.033 | 0.036 | 0.03 | 0.029 | 0.032 | 0.029 | 0.029 | 0.028 | 0.03 | 0.028 | 0.03 | 0.03 |
|  | 2F11 |  | 0.037 | 0.039 | 0.03 | 0.029 | 0.029 | 0.029 | 0.03 | 0.027 | 0.029 | 0.028 | 0.028 | 0.037 |
|  | 2A12 |  | 0.061 | 0.031 | 0.03 | 0.029 | 0.029 | 0.028 | 0.031 | 0.03 | 0.029 | 0.03 | 0.028 | 0.033 |
|  | 3F8 |  | 0.032 | 0.03 | 0.034 | 0.034 | 0.028 | 0.028 | 0.029 | 0.029 | 0.028 | 0.03 | 0.029 | 0.036 |
|  | 3C9 |  | 0.034 | 0.029 | 0.032 | 0.029 | 0.029 | 0.03 | 0.029 | 0.028 | 0.03 | 0.028 | 0.037 | 0.037 |
|  | 3F9 |  | 0.032 | 0.041 | 0.032 | 0.031 | 0.031 | 0.029 | 0.028 | 0.029 | 0.029 | 0.03 | 0.037 | 0.03 |
|  | 3A9 |  | 0.034 | 0.036 | 0.031 | 0.028 | 0.027 | 0.029 | 0.028 | 0.028 | 0.037 | 0.031 | 0.033 | 0.029 |
|  | 3B7 |  | 0.05 | 0.053 | 0.034 | 0.039 | 0.032 | 0.031 | 0.032 | 0.033 | 0.031 | 0.032 | 0.032 | 0.034 |
| Used Plate 2 | 3H7 | 21.10 | 0.948 | 0.94 | 0.248 | 0.084 | 0.135 | 0.056 | 0.094 | 0.049 | 0.05 | 0.049 | 0.046 | 0.061 |
|  | 4G2 |  | 1.226 | 2.791 | 2.002 | 0.783 | 0.272 | 0.129 | 0.073 | 0.083 | 0.061 | 0.068 | 0.041 | 0.078 |
|  | 2B9 |  | 1.125 | 2.325 | 1.531 | 0.523 | 0.158 | 0.084 | 0.082 | 0.055 | 0.104 | 0.071 | 0.055 | 0.065 |
|  | 2D7 |  | 0.132 | 0.131 | 0.085 | 0.08 | 0.063 | 0.085 | 0.131 | 0.102 | 0.091 | 0.06 | 0.063 | 0.063 |
|  | 2A9 |  | 0.101 | 0.092 | 0.104 | 0.085 | 0.076 | 0.061 | 0.066 | 0.068 | 0.067 | 0.073 | 0.066 | 0.067 |
|  | 3D10 |  | 1.346 | 2.098 | 2.081 | 2.037 | 0.697 | 0.291 | 0.096 | 0.085 | 0.541 | 0.098 | 0.085 | 0.067 |
|  | 2H8 |  | 1.058 | 1.684 | 0.651 | 0.251 | 0.091 | 0.065 | 0.052 | 0.058 | 0.051 | 0.049 | 0.048 | 0.055 |
|  | 3F7 |  | 0.921 | 0.454 | 0.165 | 0.071 | 0.064 | 0.066 | 0.057 | 0.059 | 0.055 | 0.057 | 0.055 | 0.069 |
| Fresh Plate 2 | 3H7 | 21.20 | 0.034 | 0.032 | 0.036 | 0.03 | 0.028 | 0.035 | 0.031 | 0.027 | 0.027 | 0.03 | 0.028 | 0.031 |
|  | 4G2 |  | 0.031 | 0.033 | 0.034 | 0.036 | 0.035 | 0.036 | 0.032 | 0.032 | 0.034 | 0.035 | 0.027 | 0.034 |
|  | 2B9 |  | 0.04 | 0.036 | 0.036 | 0.034 | 0.036 | 0.035 | 0.036 | 0.035 | 0.028 | 0.033 | 0.032 | 0.038 |
|  | 2D7 |  | 0.035 | 0.033 | 0.035 | 0.032 | 0.029 | 0.034 | 0.033 | 0.031 | 0.035 | 0.034 | 0.033 | 0.035 |
|  | 2A9 |  | 0.036 | 0.037 | 0.035 | 0.035 | 0.029 | 0.035 | 0.033 | 0.035 | 0.027 | 0.029 | 0.028 | 0.035 |
|  | 3D10 |  | 0.038 | 0.037 | 0.033 | 0.029 | 0.029 | 0.038 | 0.036 | 0.03 | 0.039 | 0.03 | 0.037 | 0.038 |
|  | 2H8 |  | 0.035 | 0.027 | 0.03 | 0.035 | 0.03 | 0.035 | 0.028 | 0.033 | 0.034 | 0.034 | 0.026 | 0.035 |
|  | 3F7 |  | 0.04 | 0.031 | 0.037 | 0.035 | 0.032 | 0.04 | 0.035 | 0.039 | 0.037 | 0.032 | 0.04 | 0.034 |
| Used plate 1 | 4F6 |  | 1.48 | 2.191 | 1.614 | 0.72 | 0.297 | 0.242 | 0.182 | 0.164 | 0.154 | 0.142 | 0.122 | 0.151 |
|  | 4A12 |  | 1.418 | 2.392 | 2.268 | 1.684 | 0.724 | 0.344 | 0.208 | 0.189 | 0.166 | 0.164 | 0.163 | 0.129 |
|  | 4B2 |  | 1.027 | 2.151 | 1.547 | 0.774 | 0.362 | 0.227 | 0.198 | 0.16 | 0.178 | 0.16 | 0.156 | 0.115 |
|  | 3F5 |  | 1.832 | 2.4 | 1.927 | 1.421 | 0.565 | 0.309 | 0.247 | 0.198 | 0.172 | 0.167 | 0.169 | 0.13 |
|  | 4H12 |  | 0.962 | 2.732 | 3.07 | 2.011 | 0.958 | 0.48 | 0.271 | 0.247 | 0.209 | 0.213 | 0.149 | 0.175 |
|  | 4A7 |  | 0.699 | 1.198 | 0.616 | 0.407 | 0.284 | 0.213 | 0.223 | 0.206 | 0.244 | 0.196 | 0.193 | 0.221 |
|  | 4E8 |  | 0.884 | 1.683 | 1.335 | 0.653 | 0.367 | 0.238 | 0.213 | 0.196 | 0.167 | 0.157 | 0.173 | 0.12 |
|  | #NAME? |  | 1.003 | 2.421 | 1.86 | 1.002 | 0.39 | 0.251 | 0.213 | 0.215 | 0.181 | 0.151 | 0.131 | 0.118 |
| Fresh plate1 | 4F6 |  | 0.038 | 0.036 | 0.027 | 0.03 | 0.032 | 0.029 | 0.034 | 0.033 | 0.036 | 0.043 | 0.038 | 0.042 |
|  | 4A12 |  | 0.044 | 0.037 | 0.036 | 0.038 | 0.036 | 0.036 | 0.035 | 0.036 | 0.035 | 0.038 | 0.036 | 0.038 |
|  | 4B2 |  | 0.042 | 0.048 | 0.037 | 0.037 | 0.037 | 0.037 | 0.036 | 0.037 | 0.037 | 0.036 | 0.033 | 0.035 |
|  | 3F5 |  | 0.045 | 0.036 | 0.038 | 0.038 | 0.037 | 0.038 | 0.032 | 0.038 | 0.036 | 0.037 | 0.037 | 0.032 |
|  | 4H12 |  | 0.039 | 0.037 | 0.08 | 0.044 | 0.037 | 0.028 | 0.035 | 0.027 | 0.029 | 0.036 | 0.034 | 0.036 |
|  | 4A7 |  | 0.042 | 0.035 | 0.04 | 0.039 | 0.04 | 0.036 | 0.039 | 0.04 | 0.038 | 0.04 | 0.036 | 0.046 |
|  | 4E8 |  | 0.037 | 0.04 | 0.04 | 0.034 | 0.037 | 0.033 | 0.033 | 0.028 | 0.029 | 0.034 | 0.028 | 0.037 |
|  | #NAME? |  | 0.045 | 0.035 | 0.037 | 0.035 | 0.032 | 0.04 | 0.031 | 0.031 | 0.039 | 0.032 | 0.034 | 0.032 |
| Used plate 2 | 3F6 |  | 0.955 | 2.57 | 1.984 | 0.82 | 0.321 | 0.239 | 0.197 | 0.161 | 0.143 | 0.133 | 0.137 | 0.153 |
|  | 4A2 |  | 1.054 | 2.082 | 2.966 | 2.458 | 1.232 | 0.559 | 0.248 | 0.193 | 0.171 | 0.148 | 0.13 | 0.16 |
|  | 4E7 |  | 1.011 | 1.908 | 2.214 | 0.891 | 0.374 | 0.236 | 0.155 | 0.169 | 0.159 | 0.145 | 0.13 | 0.158 |
|  | 4C8 |  | 0.409 | 1.067 | 0.466 | 0.201 | 0.221 | 0.191 | 0.166 | 0.176 | 0.151 | 0.143 | 0.117 | 0.146 |
|  | 3F3 |  | 0.909 | 2.13 | 2.148 | 1.112 | 0.535 | 0.228 | 0.179 | 0.123 | 0.101 | 0.125 | 0.102 | 0.099 |
|  | 3B4 |  | 0.803 | 2.1 | 1.984 | 1.095 | 0.426 | 0.169 | 0.125 | 0.103 | 0.107 | 0.104 | 0.114 | 0.12 |
|  | 3E10 |  | 0.286 | 0.774 | 0.35 | 0.166 | 0.126 | 0.116 | 0.115 | 0.106 | 0.095 | 0.105 | 0.092 | 0.093 |
|  | 3D6 |  | 0.362 | 0.921 | 0.342 | 0.206 | 0.172 | 0.164 | 0.123 | 0.104 | 0.119 | 0.099 | 0.101 | 0.134 |
| Fresh plate 2 | 3F6 |  | 0.046 | 0.031 | 0.032 | 0.037 | 0.032 | 0.035 | 0.04 | 0.04 | 0.039 | 0.038 | 0.031 | 0.037 |
|  | 4A2 |  | 0.041 | 0.038 | 0.038 | 0.037 | 0.037 | 0.036 | 0.036 | 0.035 | 0.037 | 0.037 | 0.037 | 0.039 |
|  | 4E7 |  | 0.039 | 0.038 | 0.037 | 0.04 | 0.036 | 0.038 | 0.037 | 0.037 | 0.038 | 0.037 | 0.033 | 0.038 |

TABLE 2-continued

|   | Temperature | 1 | 2 | 3 | 4 | 5 | 6 | 7 | 8 | 9 | 10 | 11 | 12 |
|---|---|---|---|---|---|---|---|---|---|---|---|---|---|
| | 4C8 | 0.041 | 0.039 | 0.038 | 0.039 | 0.038 | 0.038 | 0.037 | 0.041 | 0.037 | 0.037 | 0.039 | 0.038 |
| | 3F3 | 0.039 | 0.04 | 0.037 | 0.037 | 0.036 | 0.037 | 0.036 | 0.037 | 0.036 | 0.039 | 0.036 | 0.037 |
| | 3B4 | 0.084 | 0.041 | 0.04 | 0.04 | 0.039 | 0.04 | 0.039 | 0.039 | 0.039 | 0.04 | 0.038 | 0.039 |
| | 3E10 | 0.04 | 0.038 | 0.038 | 0.038 | 0.037 | 0.038 | 0.037 | 0.038 | 0.037 | 0.037 | 0.036 | 0.038 |
| | 3D6 | 0.046 | 0.046 | 0.041 | 0.04 | 0.041 | 0.039 | 0.039 | 0.037 | 0.037 | 0.032 | 0.036 | 0.039 |
| Used plate3 | 4C9 | 1.231 | 3.218 | 2.996 | 2.289 | 1.078 | 0.442 | 0.264 | 0.188 | 0.172 | 0.164 | 0.183 | 0.18 |
| | 3A10 | 1.379 | 2.816 | 2.086 | 1.231 | 0.528 | 0.298 | 0.212 | 0.197 | 0.174 | 0.164 | 0.153 | 0.163 |
| | 4D7 | 1.269 | 2.895 | 2.797 | 2.234 | 1.13 | 0.503 | 0.257 | 0.202 | 0.214 | 0.177 | 0.167 | 0.18 |
| | 4D6 | 0.953 | 1.407 | 0.78 | 0.427 | 0.278 | 0.258 | 0.218 | 0.183 | 0.195 | 0.189 | 0.162 | 0.169 |
| | | 0.038 | 0.03 | 0.045 | 0.033 | 0.037 | 0.037 | 0.037 | 0.038 | 0.037 | 0.031 | 0.03 | 0.035 |
| | | 0.034 | 0.031 | 0.039 | 0.032 | 0.03 | 0.034 | 0.03 | 0.03 | 0.033 | 0.031 | 0.045 | 0.043 |
| | | 0.031 | 0.03 | 0.031 | 0.03 | 0.03 | 0.037 | 0.029 | 0.035 | 0.042 | 0.033 | 0.033 | 0.032 |
| | | 0.031 | 0.034 | 0.031 | 0.032 | 0.039 | 0.037 | 0.03 | 0.037 | 0.037 | 0.029 | 0.029 | 0.033 |
| Fresh plate 3 | 4C9 | 0.105 | 0.049 | 0.033 | 0.041 | 0.038 | 0.035 | 0.035 | 0.03 | 0.03 | 0.039 | 0.037 | 0.038 |
| | 3A10 | 0.115 | 0.046 | 0.038 | 0.037 | 0.028 | 0.034 | 0.03 | 0.032 | 0.04 | 0.04 | 0.03 | 0.035 |
| | 4D7 | 0.111 | 0.053 | 0.04 | 0.031 | 0.038 | 0.036 | 0.036 | 0.036 | 0.036 | 0.038 | 0.036 | 0.031 |
| | 4D6 | 0.069 | 0.059 | 0.042 | 0.028 | 0.028 | 0.042 | 0.041 | 0.045 | 0.039 | 0.038 | 0.038 | 0.037 |
| | | 0.037 | 0.036 | 0.041 | 0.031 | 0.031 | 0.033 | 0.036 | 0.032 | 0.032 | 0.031 | 0.038 | 0.039 |
| | | 0.037 | 0.037 | 0.037 | 0.049 | 0.035 | 0.035 | 0.031 | 0.034 | 0.033 | 0.05 | 0.038 | 0.038 |
| | | 0.033 | 0.035 | 0.036 | 0.036 | 0.037 | 0.037 | 0.031 | 0.036 | 0.038 | 0.041 | 0.032 | 0.037 |
| | | 0.03 | 0.032 | 0.029 | 0.033 | 0.03 | 0.034 | 0.035 | 0.03 | 0.029 | 0.035 | 0.022 | 0.033 |

The clone indicated as "#NAME?" in table 2 corresponds to clone 1×2.

All positive clones were collected for validating the binding to YKL-40.

Secondary Screening—Validation of Binding to YKL-40

After phage rescue supernatants containing selected single-domain antibodies were applied in ELISA to test for binding to YKL40. Serum free media (RPMI 1640 with 1% Non-essential amino acids) were conditioned by growing MG63 cell line for 4 days. The supernatant was coated in ELISA plates. Fresh media without conditioning with MG63 were used as controls.

An ELISA were performed with the PEG precipitated phage from above (obtained under the section "Dilution series of the PEG precipitated phages"):
one plate were coated using conditioned MG63 media containing YKL-40 ("used")
one plate was coated with fresh media ("fresh media")
one plate was coated with 0.5 µg purified YKL-40 from a different preparation compared to the preparation used for the screening ("YKL-40")

The ELISA were performed as above. The results are shown in Table 3 below. The first plate indicate the tested phages and their corresponding well. Row G column 5 to row H column 12 do not contain any phages and can be used as control wells.

TABLE 3

|   | 1 | 2 | 3 | 4 | 5 | 6 | 7 | 8 | 9 | 10 | 11 | 12 |
|---|---|---|---|---|---|---|---|---|---|---|---|---|
| A | 4C2 | 2F11 | 2A12 | 3F8 | 3C9 | 3F9 | 3A9 | 3B78 | 3H7 | 4G2 | 2B9 | 2D7 |
| B | 2A9 | 3D10 | 2H8 | 3F7 | 4F6 | 4A12 | 4B2 | 3F5 | 4H12 | 4A7 | 4E8 | #NAME? |
| C | 3F6 | 4A2 | 4E7 | 4C8 | 3F3 | 3B4 | 3E10 | 3D6 | 4C9 | 3A10 | 4D7 | 4D6 |
| D | 3C4 | 4E9 | 4B10 | 4D9 | 4B6 | 2F6 | 3A11 | 3B5 | 4G1 | 4H3 | 3E4 | 4G5 |
| E | 4F3 | 3A5 | 2H5 | 4C6 | 4E5 | 4D4 | 4F11 | 3F11 | 2H2 | 4F4 | 4B5 | 2F8 |
| F | 2D3 | 2B8 | 2F4 | 2C7 | 4D11 | 3F12 | 4C1 | 4E10 | 4D5 | 4B11 | 3B2 | 2A3 |
| G | 3H1 | 2H1 | 2D4 | 2C5 | | | | | | | | |
| H | | | | | | | | | | | | |
| Used Media | | | | | | | | | | | | |
| A | 2.113 | 1.965 | 1.722 | 0.055 | 1.295 | 0.609 | 2.189 | 2.199 | 0.88 | 2.081 | 1.877 | 0.134 |
| B | 0.138 | 2.187 | 1.211 | 0.499 | 2.091 | 1.86 | 1.943 | 2.018 | 1.695 | 1.676 | 1.959 | 1.765 |
| C | 2.218 | 2.185 | 2.012 | 1.391 | 1.815 | 1.814 | 1.225 | 1.506 | 1.907 | 1.888 | 1.794 | 1.022 |
| D | 0.1 | 1.55 | 2.165 | 1.579 | 1.937 | 1.851 | 1.4 | 0.138 | 2.056 | 2.01 | 1.527 | 0.69 |
| E | 2.043 | 1.589 | 2.318 | 1.93 | 1.795 | 1.805 | 1.259 | 0.513 | 2.154 | 1.898 | 0.765 | 0.768 |
| F | 1.239 | 1.672 | 1.428 | 0.078 | 1.692 | 1.805 | 2.044 | 2.149 | 2.052 | 1.998 | 2.056 | 1.99 |
| G | 2.374 | 2.003 | 2.313 | 2.214 | 0.077 | 0.055 | 0.068 | 0.226 | 0.063 | 0.059 | 0.061 | 0.054 |
| H | 0.065 | 0.06 | 0.054 | 0.079 | 0.061 | 0.063 | 0.05 | 0.064 | 0.052 | 0.054 | 0.054 | 0.056 |
| Fresh Media | | | | | | | | | | | | |
| A | 0.066 | 0.096 | 0.063 | 0.046 | 0.088 | 0.053 | 0.033 | 0.033 | 0.032 | 0.032 | 0.03 | 0.082 |
| B | 0.049 | 0.047 | 0.045 | 0.039 | 0.048 | 0.033 | 0.03 | 0.029 | 0.037 | 0.03 | 0.035 | 0.034 |
| C | 0.037 | 0.037 | 0.047 | 0.049 | 0.038 | 0.034 | 0.033 | 0.039 | 0.036 | 0.029 | 0.029 | 0.033 |
| D | 0.043 | 0.037 | 0.044 | 0.051 | 0.038 | 0.033 | 0.034 | 0.037 | 0.031 | 0.029 | 0.03 | 0.034 |
| E | 0.057 | 0.042 | 0.049 | 0.037 | 0.052 | 0.036 | 0.031 | 0.031 | 0.03 | 0.029 | 0.03 | 0.029 |
| F | 0.049 | 0.044 | 0.066 | 0.036 | 0.049 | 0.037 | 0.037 | 0.033 | 0.033 | 0.034 | 0.033 | 0.031 |
| G | 0.059 | 0.057 | 0.066 | 0.051 | 0.03 | 0.042 | 0.029 | 0.029 | 0.03 | 0.032 | 0.029 | 0.029 |
| H | 0.032 | 0.036 | 0.039 | 0.032 | 0.032 | 0.125 | 0.063 | 0.038 | 0.033 | 0.032 | 0.032 | 0.032 |
| YKL-40 | | | | | | | | | | | | |
| A | 0.075 | 0.05 | 0.054 | 0.044 | 0.041 | 0.049 | 0.048 | 0.047 | 0.038 | 0.038 | 0.038 | 0.122 |
| B | 0.068 | 0.081 | 0.038 | 0.054 | 0.064 | 0.128 | 0.04 | 0.08 | 0.136 | 0.043 | 0.046 | 0.138 |

TABLE 3-continued

|   | 1 | 2 | 3 | 4 | 5 | 6 | 7 | 8 | 9 | 10 | 11 | 12 |
|---|---|---|---|---|---|---|---|---|---|----|----|----|
| C | 0.068 | 0.523 | 0.057 | 0.045 | 0.078 | 0.054 | 0.036 | 0.037 | 0.045 | 0.04 | 0.061 | 0.104 |
| D | 0.064 | 0.052 | 0.074 | 0.074 | 0.108 | 0.232 | 0.034 | 0.032 | 0.139 | 0.115 | 0.033 | 0.033 |
| E | 0.192 | 0.052 | 0.05 | 0.045 | 0.047 | 0.035 | 0.038 | 0.035 | 0.037 | 0.032 | 0.051 | 0.049 |
| F | 0.072 | 0054 | 0.051 | 0.043 | 0.051 | 0.071 | 0.05 | 0.076 | 0.085 | 0.037 | 0.063 | 0.054 |
| G | 0.085 | 0.089 | 0.059 | 0.057 | 0.037 | 0.029 | 0.029 | 0.037 | 0.029 | 0.03 | 0.029 | 0.029 |
| H | 0.032 | 0.041 | 0.038 | 0.033 | 0.034 | 0.04 | 0.05 | 0.052 | 0.044 | 0.031 | 0.031 | 0.031 |

The clone indicated as "#NAME?" in table 3 corresponds to clone 1×2.

Phage antibodies with a signal higher than the background signal in the empty wells (Row G column 5 to row H column 12) were considered positive. A number of phage antibodies, indicated in gray, showed significant binding to purified YKL40 and were selected as the best candidates.

Sequencing of Antibodies

All the clones validated to bind to YKL40 were next sequenced. The Predator phage antibody library is a single scaffold domain library with variation in CDR2 and CDR3. Thus, the CDR1 did not vary within the YKL-40 binding clones. The sequence of each clone validated to bind to YKL40 is shown in Table 4.

TABLE 4

| Clone | Peptide sequence | SEQ ID NO |
|---|---|---|
| 4A2 | LLLLAAQPAMAEVQLLESGGGLVQPGGSLRLSC AASGFRDSDEDMGWVRQAPGKGLEWVSSISTS DGSTYYADSVKGRFTISRDNSKNTLYLQMNSLR AEDTAVYYCASQYDTGYSFDYWGQGTLVTVSSA AAAEQKLISEEDLNGAATVESCLAKPHTENSFTNV | SEQ ID NO: 2 |
| 4G1 | LLLLAAQPAMAEVQLLESGGGLVQPGGSLRLSC AASGFRDSDEDMGWVRQAPGKGLEWVSSIGDE SGSTYYADSVKGRFTISRDNSKNTLYLQNSLRAE DTAVYYCASTSDSYWSFDYWGQGTLVTVSSAA AEQKLISEEDLNGAATVESCLAKPHTENSFTNV | SEQ ID NO: 3 |
| 4H3 | LLLAAQPAMAEVQLLESGGGLVQPGGSLRLSCA ASGFRDSDEDMGWVRQAPGKGLEWVSSINAPD GSTYYADSVKGRFTISRDNSKNTLYLQMNSLRAE DTAVYYCASQWDDGYAFDYWGQGTLVTVSSAA AEQKLISEEDLNGAATVESCLAKPHTENSFTNVW | SEQ ID NO: 4 |
| 4D6 | LLLLAAQPAMAEVQLLESGGGLVQPGGSLRLSC AASGFRDSDEDMGWVRQAPGKGLEWVSSISGS DGSTYYADSVKGRFTISRDNSKNTLYLQMNSLR AEDTAVYYCASTDYLRSSFDYWGQGTLVTVSSA AAEQKLISEEDLNGAATVESCLAKPHTENSFTNV | SEQ ID NO: 5 |
| 4B6 | LLLLAAQPAMAEVQLLESGGGLVQPGGSLRLSC AASGFRDSDEDMGWVRQAPGKGLEWVSSINNS GGSTYYADSVKGRFTISRDNSKNTLYLQMNSLR AEDTAVYYCASTDWNYSFDYWGQGTLVTVSS AAAEQKLISEEDLNGAATVESCLAKPHTENSFTNV | SEQ ID NO: 6 |
| 4A12 | LLLLAAQPAMAEVQLLESGGGLVQPGGSLRLSC AASGFRDSDEDMGWVRQAPGKGLEWVSSISAE SGSTYYADSVKGRFTISRDNSKNTLYLQMNSLRA EDTAVYYCASQYGAYHDFDYWGQGTLVTVSSA AAEQKLISEEDLNGAATVESCLAKPHTENSFTNV | SEQ ID NO: 7 |
| 1X2 | LLLLAAQPAMAEVQLLESGGGLVQPGGSLRLSC AASGFRDSDEDMGWVRQAPGKGLEWVSSINYN SGSTYYADSVKGRFTISRDNSKNTLYLQMNSLR AEDTAVYYCASTPNLSSFDYWGQGTLVTVSSAA AEQKLISEEDLNGAATVESCLAKPHTENSFTNV | SEQ ID NO: 8 |
| 2F6 | LLLLAAQPAMAEVQLLESGGGLVQPGGSLRLSC AASGFRDSDEDMGWVRQAPGKGLEWVSSISDE DGSTYYADSVKGRFTISRDNSKNTLYLQMNSLR AEDTAVYYCASSGDWWYGFDYWGQGTLVTVSS AAAEQKLISEEDLNGAATVESCLAKPHTENSFTNV | SEQ ID NO: 9 |
| 2D7 | LLLLAAQPAMAEVQLLESGGGLVQPGGSLRLSC AASGFRDSDEDMGWVRQAPGKGLEWVSSISGE SGSTYYADSVKGRFTISRDNSKNTLYLQMNSLRA EDTAVYYCASVDPLDTYFDYWGQGTLVTVSSAA AEQKLISEEDLNGAATVESCLAKPHTENSFTNV | SEQ ID NO: 10 |
| 4F3 | LLLLAAQPAMAEVQLLESGGGLVQPGGSLRLSC AASGFRDSDEDMGWVRQAPGKGLEWVSSIQSS DGSTYYADSVKGRFTISRDNSKNTLYLQMNSLR AEDTAVYYCASSSQNGYVFDYWGQGTLVTVSS AAAEQKLISEEDLNGAATVESCLAKPHTENSFTNV | SEQ ID NO: 11 |
| 2H12 | LLLLAAQPAMAEVQLLESGGGLVQPGGSLRLSC AASGFRDSDEDMGWVRQAPGKGLEWVSSINNE SGSTYYADSVKGRFTISRDNSKNTLYLQMNSLRA EDTAVYYCASTSYYGFDFDYWGQGTLVTVSSAA AEQKLISEEDLNGAATVESCLAKPHTENSFTNV | SEQ ID NO: 12 |
| 2B8 | LLLLAAQPAMAEVQLLESGGGLVQPGGSLRLSC AASGFRDSDEDMGWVRQAPGKGLEWVSSIYAP NGSTYYADSVKGRFTISRDNSKNTLYLQMNSLR AEDTAVYYCASNTYDAFDYWGQGTLVTVSSAAA EQKLISEEDLNGAATVESCLAKPHTENSFTNVWK | SEQ ID NO: 13 |
| 4D9 | LLLLAAQPAMAEVQLLESGGGLVQPGGSLRLSC AASGFRDSDEDMGWVRQAPGKGLEWVSSIASD SGSTYYADSVKGRFTISRDNSKNTLYLQMNSLRA EDTAVYYCASSGYAGTVFDYWGQGTLVTVSSAA AEQKLISEEDLNGAATVESCLAKPHTENSFTNVW KDDKTLDRYANYEGCLWNATGVVVCT | SEQ ID NO: 14 |
| 2F3 | LLLLAAQPAMAEVQLLESGGGLVQPGGSLRLSC AASGFRDSDEDMGWVRQAPGKGLEWVSSIGAG SGSTYYADSVKGRFTISRDNSKNTLYLQMNSLRA EDTAVYYCASSTDARWQFDYWGQGTLVTVSSA AAEQKLISEEDLNGAATVESCLAKPHTENSFTNV. | SEQ ID NO: 15 |
| 3F12 | LLLLAAQPAMAEVQLLESGGGLVQPGGSLRLSC AASGFRDSDEDMGWVRQAPGKGLEWVSSINAN DGSTYYADSVKGRFTISRDNSKNTLYLQMNSLR AEDTAVYYCASQYDDEFAFDYWGQGTLVTVSSA AAEQKLISEEDLNGAATVESCLAKPHTENSFTNV | SEQ ID NO: 16 |
| 4D5 | LLLLAAQPAMAEVQLLESGGGLVQPGGSLRLSC AASGFRDSDEDMGWVRQAPGKGLEWVSSIGNY NGSTYYADSVKGRFTISRDNSKNTLYLQMNSLR AEDTAVYYCASVSDSGFSFDYWGQGTLVTVSSA AAEQKLISEEDLNGAATVESCLAKPHTENSFTNV. | SEQ ID NO: 17 |
| 4E10 | LLLLAAQPAMAEVQLLESGGGLVQPGGSLRLSC AASGFRDSDEDMGWVRQAPGKGLEWVSSIYGP SGSTYYADSVKGRFTISRDNSKNTLYLQMNSLRA EDTAVYYCASSDWDGYSFDYWGQGTLVTVSSA AAEQKLISEEDLNGAATVESCLAKPHTENSFTNV. | SEQ ID NO: 18 |
| 2D3 | LLLLAAQPAMAEVQLLESGGGLVQPGGSLRLSC AASGFRDSDEDMGWVRQAPGKGLEWVSSIDAE | SEQ ID NO: 19 |

TABLE 4-continued

| Clone | Peptide sequence | SEQ ID NO |
|---|---|---|
| | DGSTYYADSVKGRFTISRDNSKNTLYLQMNSLR AEDTAVYYCASQDGAYYTFDYWGQGTLVTVSSA AAEQKLISEEDLNGAATVESCLAKPHTENSFTNV | 5 |

Cloning

The two clones 4A2 and 4A12 can be cloned into a vector pFuse-hIgG2 as described in Moutel et al., 2009, or a vector containing another Immunoglobulin constant part. The vectors can be transfected into a suitable cell, such as ExpiCHO cells and expressed. Thus, leading to antibodies of $V_H$ domains fused to human IgG2 or other Fc regions expressed by the vector.

After transient transfection of suitable cells with the expression plasmid, secreted antibodies can be purified from the supernatant.

REFERENCES

Brockmann E C, Akter S, Savukoski T, Huovinen T, Lehmusvuori A et al. (2011) Synthetic single-framework antibody library integrated with rapid affinity maturation by VL shuffling. Protein Eng Des Sel 24:691-700. doi: 10.1093/protein/gzr023. PubMed: 21680620.

Christ D, Famm K, Winter G (2007) Repertoires of aggregation resistant human antibody domains. Protein Eng Des Sel 20: 413-416. doi:10.1093/protein/gzm037. PubMed: 17720749.

Fellouse F A, Esaki K, Birtalan S, Raptis D, Cancasci V J et al. (2007) High-throughput generation of synthetic antibodies from highly functional minimalist phage-displayed libraries. J Mol Biol 373: 924-940. doi:10.1016/j.jmb.2007.08.005. PubMed: 17825836.

Hust M, Dübel S (2004) Mating antibody phage display with proteomics. Trends Biotechnol 22: 8-14. doi:10.1016/j.tibtech.2003.10.011. PubMed: 14690617.

Johansen et al., 1992. Identifications of proteins secreted by human osteoblastic cells in culture. J Bone Miner Res, 7:501-512, 1992.

Mandrup, O. A., N. A. Friis, S. Lykkemark, J. Just and P. Kristensen (2013). "A novel heavy domain antibody library with functionally optimized complementarity determining regions." *PLoS One* 8(10): e76834.

Moutel, S., A. El Marjou, O. Vielemeyer, C. Nizak, P. Benaroch, S. Dubel and F. Perez (2009). "A multi-Fc-species system for recombinant antibody production." *BMC Biotechnol* 9: 14.

Pansri P, Jaruseranee N, Rangnoi K, Kristensen P, Yamabhai M (2009) A compact phage display human scFv library for selection of antibodies to a wide variety of antigens. BMC Biotechnol 9: 6. doi:10.1186/1472-6750-9-6. PubMed: 19175944.

Rothe C, Urlinger S, Löhning C, Prassler J, Stark Y et al. (2008) The human combinatorial antibody library HuCAL GOLD combines diversification of all six CDRs according to the natural immune system with a novel display method for efficient selection of high-affinity antibodies. J Mol Biol 376: 1182-1200. doi:10.1016/j.jmb.2007.12.018. PubMed: 18191144.

Silacci M, Brack S, Schirru G, Målind J, Ettore A et al. (2005) Design, construction, and characterization of a large synthetic human antibody phage display library. Proteomics 5: 2340-2350. doi:10.1002/pmic. 200401273. PubMed: 15880779.

The invention claimed is:

1. A YKL-40 antibody comprising a variable region comprising a CDR1, CDR2 and CDR3, wherein
    CDR1 comprises or consists of amino acid sequence FRDSDEDMG (SEQ ID NO:20);
    CDR2 comprises or consists of amino acid sequence SISTSDGSTYY (SEQ ID NO:56); and
    CDR3 comprises or consists of amino acid sequence QYDTGYSFDY (SEQ ID NO:57).

2. The YKL-40 antibody according to claim 1, wherein said variable region comprises or consists of a $V_H$ domain.

3. The YKL-40 antibody according to claim 1, wherein said variable region is linked to an Fc region, optionally via a linker.

4. The YKL-40 antibody according to claim 1, wherein said YKL-40 antibody comprises or consists of two variable regions, wherein each variable region is linked to an Fc region, optionally by a linker, wherein said Fc regions are linked to each other.

5. The YKL-40 antibody according to claim 4, wherein said Fc regions are linked together by disulphide bonds.

6. The YLK-40 antibody according to claim 1, wherein the antibody comprises or consists of a variable region comprising or consisting of amino acid sequence SEQ ID NO:2.

7. The YLK-40 antibody according to claim 1, wherein the antibody comprises a variable region consisting of amino acid sequence SEQ ID NO:2.

8. The YLK-40 antibody according to claim 1, wherein the antibody consists of a variable region consisting of amino acid sequence SEQ ID NO:2 linked to an Fc region, wherein said antibody optionally forms dimers.

9. The YKL-40 antibody according to claim 3, wherein the Fc region is a human Fc region.

10. The YKL-40 antibody according to claim 3, wherein the Fc region comprises or consists of amino acid sequence SEQ ID NO:58 or SEQ ID NO:59.

* * * * *

SEQUENCE LISTING

```
<160> NUMBER OF SEQ ID NOS: 59

<210> SEQ ID NO 1
<211> LENGTH: 383
<212> TYPE: PRT
<213> ORGANISM: Homo sapiens

<400> SEQUENCE: 1

Met Gly Val Lys Ala Ser Gln Thr Gly Phe Val Val Leu Val Leu Leu
1               5                   10                  15

Gln Cys Cys Ser Ala Tyr Lys Leu Val Cys Tyr Tyr Thr Ser Trp Ser
                20                  25                  30

Gln Tyr Arg Glu Gly Asp Gly Ser Cys Phe Pro Asp Ala Leu Asp Arg
            35                  40                  45

Phe Leu Cys Thr His Ile Ile Tyr Ser Phe Ala Asn Ile Ser Asn Asp
        50                  55                  60

His Ile Asp Thr Trp Glu Trp Asn Asp Val Thr Leu Tyr Gly Met Leu
65                  70                  75                  80

Asn Thr Leu Lys Asn Arg Asn Pro Asn Leu Lys Thr Leu Leu Ser Val
                85                  90                  95

Gly Gly Trp Asn Phe Gly Ser Gln Arg Phe Ser Lys Ile Ala Ser Asn
                100                 105                 110

Thr Gln Ser Arg Arg Thr Phe Ile Lys Ser Val Pro Pro Phe Leu Arg
            115                 120                 125

Thr His Gly Phe Asp Gly Leu Asp Leu Ala Trp Leu Tyr Pro Gly Arg
        130                 135                 140
```

Arg Asp Lys Gln His Phe Thr Thr Leu Ile Lys Glu Met Lys Ala Glu
145                 150                 155                 160

Phe Ile Lys Glu Ala Gln Pro Gly Lys Lys Gln Leu Leu Leu Ser Ala
                165                 170                 175

Ala Leu Ser Ala Gly Lys Val Thr Ile Asp Ser Ser Tyr Asp Ile Ala
            180                 185                 190

Lys Ile Ser Gln His Leu Asp Phe Ile Ser Ile Met Thr Tyr Asp Phe
            195                 200                 205

His Gly Ala Trp Arg Gly Thr Thr Gly His His Ser Pro Leu Phe Arg
        210                 215                 220

Gly Gln Glu Asp Ala Ser Pro Asp Arg Phe Ser Asn Thr Asp Tyr Ala
225                 230                 235                 240

Val Gly Tyr Met Leu Arg Leu Gly Ala Pro Ala Ser Lys Leu Val Met
                245                 250                 255

Gly Ile Pro Thr Phe Gly Arg Ser Phe Thr Leu Ala Ser Ser Glu Thr
            260                 265                 270

Gly Val Gly Ala Pro Ile Ser Gly Pro Gly Ile Pro Gly Arg Phe Thr
        275                 280                 285

Lys Glu Ala Gly Thr Leu Ala Tyr Tyr Glu Ile Cys Asp Phe Leu Arg
290                 295                 300

Gly Ala Thr Val His Arg Ile Leu Gly Gln Gln Val Pro Tyr Ala Thr
305                 310                 315                 320

Lys Gly Asn Gln Trp Val Gly Tyr Asp Asp Gln Glu Ser Val Lys Ser
                325                 330                 335

Lys Val Gln Tyr Leu Lys Asp Arg Gln Leu Ala Gly Ala Met Val Trp
            340                 345                 350

Ala Leu Asp Leu Asp Asp Phe Gln Gly Ser Phe Cys Gly Gln Asp Leu
            355                 360                 365

Arg Phe Pro Leu Thr Asn Ala Ile Lys Asp Ala Leu Ala Ala Thr
        370                 375                 380

<210> SEQ ID NO 2
<211> LENGTH: 165
<212> TYPE: PRT
<213> ORGANISM: Artificial sequence
<220> FEATURE:
<223> OTHER INFORMATION: Human single domain antibody

<400> SEQUENCE: 2

Leu Leu Leu Leu Ala Ala Gln Pro Ala Met Ala Glu Val Gln Leu Leu
1               5                   10                  15

Glu Ser Gly Gly Gly Leu Val Gln Pro Gly Gly Ser Leu Arg Leu Ser
                20                  25                  30

Cys Ala Ala Ser Gly Phe Arg Asp Ser Asp Glu Asp Met Gly Trp Val
            35                  40                  45

Arg Gln Ala Pro Gly Lys Gly Leu Glu Trp Val Ser Ser Ile Ser Thr
        50                  55                  60

Ser Asp Gly Ser Thr Tyr Tyr Ala Asp Ser Val Lys Gly Arg Phe Thr
65                  70                  75                  80

Ile Ser Arg Asp Asn Ser Lys Asn Thr Leu Tyr Leu Gln Met Asn Ser
                85                  90                  95

Leu Arg Ala Glu Asp Thr Ala Val Tyr Tyr Cys Ala Ser Gln Tyr Asp
            100                 105                 110

Thr Gly Tyr Ser Phe Asp Tyr Trp Gly Gln Gly Thr Leu Val Thr Val
        115                 120                 125

```
Ser Ser Ala Ala Ala Glu Gln Lys Leu Ile Ser Glu Asp Leu Asn
    130                 135                 140

Gly Ala Ala Thr Val Glu Ser Cys Leu Ala Lys Pro His Thr Glu Asn
145                 150                 155                 160

Ser Phe Thr Asn Val
                165

<210> SEQ ID NO 3
<211> LENGTH: 164
<212> TYPE: PRT
<213> ORGANISM: Artificial sequence
<220> FEATURE:
<223> OTHER INFORMATION: Human single domain antibody

<400> SEQUENCE: 3

Leu Leu Leu Leu Ala Ala Gln Pro Ala Met Ala Glu Val Gln Leu Leu
1               5                   10                  15

Glu Ser Gly Gly Gly Leu Val Gln Pro Gly Gly Ser Leu Arg Leu Ser
                20                  25                  30

Cys Ala Ala Ser Gly Phe Arg Asp Ser Asp Glu Asp Met Gly Trp Val
                35                  40                  45

Arg Gln Ala Pro Gly Lys Gly Leu Glu Trp Val Ser Ser Ile Gly Asp
            50                  55                  60

Glu Ser Gly Ser Thr Tyr Tyr Ala Asp Ser Val Lys Gly Arg Phe Thr
65                  70                  75                  80

Ile Ser Arg Asp Asn Ser Lys Asn Thr Leu Tyr Leu Gln Asn Ser Leu
                85                  90                  95

Arg Ala Glu Asp Thr Ala Val Tyr Tyr Cys Ala Ser Thr Ser Asp Ser
                100                 105                 110

Tyr Trp Ser Phe Asp Tyr Trp Gly Gln Gly Thr Leu Val Thr Val Ser
            115                 120                 125

Ser Ala Ala Ala Glu Gln Lys Leu Ile Ser Glu Glu Asp Leu Asn Gly
    130                 135                 140

Ala Ala Thr Val Glu Ser Cys Leu Ala Lys Pro His Thr Glu Asn Ser
145                 150                 155                 160

Phe Thr Asn Val

<210> SEQ ID NO 4
<211> LENGTH: 165
<212> TYPE: PRT
<213> ORGANISM: Artificial sequence
<220> FEATURE:
<223> OTHER INFORMATION: Human single domain antibody

<400> SEQUENCE: 4

Leu Leu Leu Ala Ala Gln Pro Ala Met Ala Glu Val Gln Leu Leu Glu
1               5                   10                  15

Ser Gly Gly Gly Leu Val Gln Pro Gly Gly Ser Leu Arg Leu Ser Cys
                20                  25                  30

Ala Ala Ser Gly Phe Arg Asp Ser Asp Glu Asp Met Gly Trp Val Arg
                35                  40                  45

Gln Ala Pro Gly Lys Gly Leu Glu Trp Val Ser Ser Ile Asn Ala Pro
            50                  55                  60

Asp Gly Ser Thr Tyr Tyr Ala Asp Ser Val Lys Gly Arg Phe Thr Ile
65                  70                  75                  80

Ser Arg Asp Asn Ser Lys Asn Thr Leu Tyr Leu Gln Met Asn Ser Leu
                85                  90                  95
```

```
Arg Ala Glu Asp Thr Ala Val Tyr Tyr Cys Ala Ser Gln Trp Asp
            100                 105                 110

Gly Tyr Ala Phe Asp Tyr Trp Gly Gln Gly Thr Leu Val Thr Val Ser
            115                 120                 125

Ser Ala Ala Ala Glu Gln Lys Leu Ile Ser Glu Glu Asp Leu Asn Gly
    130                 135                 140

Ala Ala Thr Val Glu Ser Cys Leu Ala Lys Pro His Thr Glu Asn Ser
145                 150                 155                 160

Phe Thr Asn Val Trp
                165

<210> SEQ ID NO 5
<211> LENGTH: 165
<212> TYPE: PRT
<213> ORGANISM: Artificial sequence
<220> FEATURE:
<223> OTHER INFORMATION: Human single domain antibody

<400> SEQUENCE: 5

Leu Leu Leu Leu Ala Ala Gln Pro Ala Met Ala Glu Val Gln Leu Leu
1               5                   10                  15

Glu Ser Gly Gly Gly Leu Val Gln Pro Gly Gly Ser Leu Arg Leu Ser
            20                  25                  30

Cys Ala Ala Ser Gly Phe Arg Asp Ser Asp Glu Asp Met Gly Trp Val
            35                  40                  45

Arg Gln Ala Pro Gly Lys Gly Leu Glu Trp Val Ser Ser Ile Ser Gly
    50                  55                  60

Ser Asp Gly Ser Thr Tyr Tyr Ala Asp Ser Val Lys Gly Arg Phe Thr
65                  70                  75                  80

Ile Ser Arg Asp Asn Ser Lys Asn Thr Leu Tyr Leu Gln Met Asn Ser
                85                  90                  95

Leu Arg Ala Glu Asp Thr Ala Val Tyr Tyr Cys Ala Ser Thr Asp Tyr
            100                 105                 110

Leu Arg Ser Ser Phe Asp Tyr Trp Gly Gln Gly Thr Leu Val Thr Val
            115                 120                 125

Ser Ser Ala Ala Ala Glu Gln Lys Leu Ile Ser Glu Glu Asp Leu Asn
    130                 135                 140

Gly Ala Ala Thr Val Glu Ser Cys Leu Ala Lys Pro His Thr Glu Asn
145                 150                 155                 160

Ser Phe Thr Asn Val
                165

<210> SEQ ID NO 6
<211> LENGTH: 165
<212> TYPE: PRT
<213> ORGANISM: Artificial sequence
<220> FEATURE:
<223> OTHER INFORMATION: Human single domain antibody

<400> SEQUENCE: 6

Leu Leu Leu Leu Ala Ala Gln Pro Ala Met Ala Glu Val Gln Leu Leu
1               5                   10                  15

Glu Ser Gly Gly Gly Leu Val Gln Pro Gly Gly Ser Leu Arg Leu Ser
            20                  25                  30

Cys Ala Ala Ser Gly Phe Arg Asp Ser Asp Glu Asp Met Gly Trp Val
            35                  40                  45

Arg Gln Ala Pro Gly Lys Gly Leu Glu Trp Val Ser Ser Ile Asn Asn
```

```
Ser Gly Gly Ser Thr Tyr Tyr Ala Asp Ser Val Lys Gly Arg Phe Thr
65                  70                  75                  80

Ile Ser Arg Asp Asn Ser Lys Asn Thr Leu Tyr Leu Gln Met Asn Ser
                85                  90                  95

Leu Arg Ala Glu Asp Thr Ala Val Tyr Tyr Cys Ala Ser Thr Tyr Asp
                100                 105                 110

Trp Asn Tyr Ser Phe Asp Tyr Trp Gly Gln Gly Thr Leu Val Thr Val
            115                 120                 125

Ser Ser Ala Ala Ala Glu Gln Lys Leu Ile Ser Glu Glu Asp Leu Asn
            130                 135                 140

Gly Ala Ala Thr Val Glu Ser Cys Leu Ala Lys Pro His Thr Glu Asn
145                 150                 155                 160

Ser Phe Thr Asn Val
                165
```

<210> SEQ ID NO 7
<211> LENGTH: 165
<212> TYPE: PRT
<213> ORGANISM: Artificial sequence
<220> FEATURE:
<223> OTHER INFORMATION: Human single domain antibody

<400> SEQUENCE: 7

```
Leu Leu Leu Leu Ala Ala Gln Pro Ala Met Ala Glu Val Gln Leu Leu
1               5                   10                  15

Glu Ser Gly Gly Gly Leu Val Gln Pro Gly Gly Ser Leu Arg Leu Ser
                20                  25                  30

Cys Ala Ala Ser Gly Phe Arg Asp Ser Asp Glu Asp Met Gly Trp Val
                35                  40                  45

Arg Gln Ala Pro Gly Lys Gly Leu Glu Trp Val Ser Ser Ile Ser Ala
            50                  55                  60

Glu Ser Gly Ser Thr Tyr Tyr Ala Asp Ser Val Lys Gly Arg Phe Thr
65                  70                  75                  80

Ile Ser Arg Asp Asn Ser Lys Asn Thr Leu Tyr Leu Gln Met Asn Ser
                85                  90                  95

Leu Arg Ala Glu Asp Thr Ala Val Tyr Tyr Cys Ala Ser Gln Tyr Gly
                100                 105                 110

Ala Tyr His Asp Phe Asp Tyr Trp Gly Gln Gly Thr Leu Val Thr Val
            115                 120                 125

Ser Ser Ala Ala Ala Glu Gln Lys Leu Ile Ser Glu Glu Asp Leu Asn
            130                 135                 140

Gly Ala Ala Thr Val Glu Ser Cys Leu Ala Lys Pro His Thr Glu Asn
145                 150                 155                 160

Ser Phe Thr Asn Val
                165
```

<210> SEQ ID NO 8
<211> LENGTH: 165
<212> TYPE: PRT
<213> ORGANISM: Artificial sequence
<220> FEATURE:
<223> OTHER INFORMATION: Human single domain antibody

<400> SEQUENCE: 8

```
Leu Leu Leu Leu Ala Ala Gln Pro Ala Met Ala Glu Val Gln Leu Leu
1               5                   10                  15
```

```
Glu Ser Gly Gly Gly Leu Val Gln Pro Gly Gly Ser Leu Arg Leu Ser
            20                  25                  30

Cys Ala Ala Ser Gly Phe Arg Asp Ser Asp Glu Asp Met Gly Trp Val
        35                  40                  45

Arg Gln Ala Pro Gly Lys Gly Leu Glu Trp Val Ser Ser Ile Asn Tyr
    50                  55                  60

Asn Ser Gly Ser Thr Tyr Tyr Ala Asp Ser Val Lys Gly Arg Phe Thr
65                  70                  75                  80

Ile Ser Arg Asp Asn Ser Lys Asn Thr Leu Tyr Leu Gln Met Asn Ser
                85                  90                  95

Leu Arg Ala Glu Asp Thr Ala Val Tyr Tyr Cys Ala Ser Thr Pro Asn
                100                 105                 110

Leu Asn Ser Ser Phe Asp Tyr Trp Gly Gln Gly Thr Leu Val Thr Val
            115                 120                 125

Ser Ser Ala Ala Ala Glu Gln Lys Leu Ile Ser Glu Glu Asp Leu Asn
        130                 135                 140

Gly Ala Ala Thr Val Glu Ser Cys Leu Ala Lys Pro His Thr Glu Asn
145                 150                 155                 160

Ser Phe Thr Asn Val
            165

<210> SEQ ID NO 9
<211> LENGTH: 165
<212> TYPE: PRT
<213> ORGANISM: Artificial sequence
<220> FEATURE:
<223> OTHER INFORMATION: Human single domain antibody

<400> SEQUENCE: 9

Leu Leu Leu Leu Ala Ala Gln Pro Ala Met Ala Glu Val Gln Leu Leu
1               5                   10                  15

Glu Ser Gly Gly Gly Leu Val Gln Pro Gly Gly Ser Leu Arg Leu Ser
            20                  25                  30

Cys Ala Ala Ser Gly Phe Arg Asp Ser Asp Glu Asp Met Gly Trp Val
        35                  40                  45

Arg Gln Ala Pro Gly Lys Gly Leu Glu Trp Val Ser Ser Ile Ser Asp
    50                  55                  60

Glu Asp Gly Ser Thr Tyr Tyr Ala Asp Ser Val Lys Gly Arg Phe Thr
65                  70                  75                  80

Ile Ser Arg Asp Asn Ser Lys Asn Thr Leu Tyr Leu Gln Met Asn Ser
                85                  90                  95

Leu Arg Ala Glu Asp Thr Ala Val Tyr Tyr Cys Ala Ser Ser Gly Asp
                100                 105                 110

Trp Trp Tyr Gly Phe Asp Tyr Trp Gly Gln Gly Thr Leu Val Thr Val
            115                 120                 125

Ser Ser Ala Ala Ala Glu Gln Lys Leu Ile Ser Glu Glu Asp Leu Asn
        130                 135                 140

Gly Ala Ala Thr Val Glu Ser Cys Leu Ala Lys Pro His Thr Glu Asn
145                 150                 155                 160

Ser Phe Thr Asn Val
            165

<210> SEQ ID NO 10
<211> LENGTH: 165
<212> TYPE: PRT
<213> ORGANISM: Artificial sequence
<220> FEATURE:
```

<223> OTHER INFORMATION: Human single domain antibody

<400> SEQUENCE: 10

Leu Leu Leu Leu Ala Ala Gln Pro Ala Met Ala Glu Val Gln Leu Leu
1               5                   10                  15

Glu Ser Gly Gly Gly Leu Val Gln Pro Gly Gly Ser Leu Arg Leu Ser
            20                  25                  30

Cys Ala Ala Ser Gly Phe Arg Asp Ser Asp Glu Asp Met Gly Trp Val
        35                  40                  45

Arg Gln Ala Pro Gly Lys Gly Leu Glu Trp Val Ser Ser Ile Ser Gly
    50                  55                  60

Glu Ser Gly Ser Thr Tyr Tyr Ala Asp Ser Val Lys Gly Arg Phe Thr
65                  70                  75                  80

Ile Ser Arg Asp Asn Ser Lys Asn Thr Leu Tyr Leu Gln Met Asn Ser
                85                  90                  95

Leu Arg Ala Glu Asp Thr Ala Val Tyr Tyr Cys Ala Ser Val Asp Pro
            100                 105                 110

Leu Asp Thr Tyr Phe Asp Tyr Trp Gly Gln Gly Thr Leu Val Thr Val
        115                 120                 125

Ser Ser Ala Ala Ala Glu Gln Lys Leu Ile Ser Glu Glu Asp Leu Asn
    130                 135                 140

Gly Ala Ala Thr Val Glu Ser Cys Leu Ala Lys Pro His Thr Glu Asn
145                 150                 155                 160

Ser Phe Thr Asn Val
                165

<210> SEQ ID NO 11
<211> LENGTH: 165
<212> TYPE: PRT
<213> ORGANISM: Artificial sequence
<220> FEATURE:
<223> OTHER INFORMATION: Human single domain antibody

<400> SEQUENCE: 11

Leu Leu Leu Leu Ala Ala Gln Pro Ala Met Ala Glu Val Gln Leu Leu
1               5                   10                  15

Glu Ser Gly Gly Gly Leu Val Gln Pro Gly Gly Ser Leu Arg Leu Ser
            20                  25                  30

Cys Ala Ala Ser Gly Phe Arg Asp Ser Asp Glu Asp Met Gly Trp Val
        35                  40                  45

Arg Gln Ala Pro Gly Lys Gly Leu Glu Trp Val Ser Ser Ile Gln Ser
    50                  55                  60

Ser Asp Gly Ser Thr Tyr Tyr Ala Asp Ser Val Lys Gly Arg Phe Thr
65                  70                  75                  80

Ile Ser Arg Asp Asn Ser Lys Asn Thr Leu Tyr Leu Gln Met Asn Ser
                85                  90                  95

Leu Arg Ala Glu Asp Thr Ala Val Tyr Tyr Cys Ala Ser Ser Ser Gln
            100                 105                 110

Asn Gly Tyr Val Phe Asp Tyr Trp Gly Gln Gly Thr Leu Val Thr Val
        115                 120                 125

Ser Ser Ala Ala Ala Glu Gln Lys Leu Ile Ser Glu Glu Asp Leu Asn
    130                 135                 140

Gly Ala Ala Thr Val Glu Ser Cys Leu Ala Lys Pro His Thr Glu Asn
145                 150                 155                 160

Ser Phe Thr Asn Val
                165

<210> SEQ ID NO 12
<211> LENGTH: 165
<212> TYPE: PRT
<213> ORGANISM: Artificial sequence
<220> FEATURE:
<223> OTHER INFORMATION: Human single domain antibody

<400> SEQUENCE: 12

```
Leu Leu Leu Leu Ala Ala Gln Pro Ala Met Ala Glu Val Gln Leu Leu
1               5                   10                  15

Glu Ser Gly Gly Gly Leu Val Gln Pro Gly Gly Ser Leu Arg Leu Ser
            20                  25                  30

Cys Ala Ala Ser Gly Phe Arg Asp Ser Asp Glu Asp Met Gly Trp Val
        35                  40                  45

Arg Gln Ala Pro Gly Lys Gly Leu Glu Trp Val Ser Ser Ile Asn Asn
    50                  55                  60

Glu Ser Gly Ser Thr Tyr Tyr Ala Asp Ser Val Lys Gly Arg Phe Thr
65                  70                  75                  80

Ile Ser Arg Asp Asn Ser Lys Asn Thr Leu Tyr Leu Gln Met Asn Ser
                85                  90                  95

Leu Arg Ala Glu Asp Thr Ala Val Tyr Tyr Cys Ala Ser Thr Ser Tyr
            100                 105                 110

Tyr Gly Phe Asp Phe Asp Tyr Trp Gly Gln Gly Thr Leu Val Thr Val
        115                 120                 125

Ser Ser Ala Ala Ala Glu Gln Lys Leu Ile Ser Glu Glu Asp Leu Asn
    130                 135                 140

Gly Ala Ala Thr Val Glu Ser Cys Leu Ala Lys Pro His Thr Glu Asn
145                 150                 155                 160

Ser Phe Thr Asn Val
                165
```

<210> SEQ ID NO 13
<211> LENGTH: 165
<212> TYPE: PRT
<213> ORGANISM: Artificial sequence
<220> FEATURE:
<223> OTHER INFORMATION: Human single domain antibody

<400> SEQUENCE: 13

```
Leu Leu Leu Leu Ala Ala Gln Pro Ala Met Ala Glu Val Gln Leu Leu
1               5                   10                  15

Glu Ser Gly Gly Gly Leu Val Gln Pro Gly Gly Ser Leu Arg Leu Ser
            20                  25                  30

Cys Ala Ala Ser Gly Phe Arg Asp Ser Asp Glu Asp Met Gly Trp Val
        35                  40                  45

Arg Gln Ala Pro Gly Lys Gly Leu Glu Trp Val Ser Ser Ile Tyr Ala
    50                  55                  60

Pro Asn Gly Ser Thr Tyr Tyr Ala Asp Ser Val Lys Gly Arg Phe Thr
65                  70                  75                  80

Ile Ser Arg Asp Asn Ser Lys Asn Thr Leu Tyr Leu Gln Met Asn Ser
                85                  90                  95

Leu Arg Ala Glu Asp Thr Ala Val Tyr Tyr Cys Ala Ser Asn Thr Tyr
            100                 105                 110

Asp Ala Phe Asp Tyr Trp Gly Gln Gly Thr Leu Val Thr Val Ser Ser
        115                 120                 125

Ala Ala Ala Glu Gln Lys Leu Ile Ser Glu Glu Asp Leu Asn Gly Ala
```

```
                130             135             140
Ala Thr Val Glu Ser Cys Leu Ala Lys Pro His Thr Glu Asn Ser Phe
145                 150                 155                 160

Thr Asn Val Trp Lys
                165

<210> SEQ ID NO 14
<211> LENGTH: 192
<212> TYPE: PRT
<213> ORGANISM: Artificial sequence
<220> FEATURE:
<223> OTHER INFORMATION: Human single domain antibody

<400> SEQUENCE: 14

Leu Leu Leu Leu Ala Ala Gln Pro Ala Met Ala Glu Val Gln Leu Leu
1               5                   10                  15

Glu Ser Gly Gly Gly Leu Val Gln Pro Gly Gly Ser Leu Arg Leu Ser
                20                  25                  30

Cys Ala Ala Ser Gly Phe Arg Asp Ser Asp Glu Asp Met Gly Trp Val
            35                  40                  45

Arg Gln Ala Pro Gly Lys Gly Leu Glu Trp Val Ser Ser Ile Ala Ser
        50                  55                  60

Asp Ser Gly Ser Thr Tyr Tyr Ala Asp Ser Val Lys Gly Arg Phe Thr
65                  70                  75                  80

Ile Ser Arg Asp Asn Ser Lys Asn Thr Leu Tyr Leu Gln Met Asn Ser
                85                  90                  95

Leu Arg Ala Glu Asp Thr Ala Val Tyr Tyr Cys Ala Ser Ser Gly Tyr
                100                 105                 110

Ala Gly Thr Val Phe Asp Tyr Trp Gly Gln Gly Thr Leu Val Thr Val
            115                 120                 125

Ser Ser Ala Ala Ala Glu Gln Lys Leu Ile Ser Glu Glu Asp Leu Asn
        130                 135                 140

Gly Ala Ala Thr Val Glu Ser Cys Leu Ala Lys Pro His Thr Glu Asn
145                 150                 155                 160

Ser Phe Thr Asn Val Trp Lys Asp Asp Lys Thr Leu Asp Arg Tyr Ala
                165                 170                 175

Asn Tyr Glu Gly Cys Leu Trp Asn Ala Thr Gly Val Val Val Cys Thr
                180                 185                 190

<210> SEQ ID NO 15
<211> LENGTH: 165
<212> TYPE: PRT
<213> ORGANISM: Artificial sequence
<220> FEATURE:
<223> OTHER INFORMATION: Human single domain antibody

<400> SEQUENCE: 15

Leu Leu Leu Leu Ala Ala Gln Pro Ala Met Ala Glu Val Gln Leu Leu
1               5                   10                  15

Glu Ser Gly Gly Gly Leu Val Gln Pro Gly Gly Ser Leu Arg Leu Ser
                20                  25                  30

Cys Ala Ala Ser Gly Phe Arg Asp Ser Asp Glu Asp Met Gly Trp Val
            35                  40                  45

Arg Gln Ala Pro Gly Lys Gly Leu Glu Trp Val Ser Ser Ile Gly Ala
        50                  55                  60

Gly Ser Gly Ser Thr Tyr Tyr Ala Asp Ser Val Lys Gly Arg Phe Thr
65                  70                  75                  80
```

```
Ile Ser Arg Asp Asn Ser Lys Asn Thr Leu Tyr Leu Gln Met Asn Ser
            85                  90                  95

Leu Arg Ala Glu Asp Thr Ala Val Tyr Tyr Cys Ala Ser Ser Thr Asp
            100                 105                 110

Ala Arg Trp Gln Phe Asp Tyr Trp Gly Gln Gly Thr Leu Val Thr Val
            115                 120                 125

Ser Ser Ala Ala Ala Glu Gln Lys Leu Ile Ser Glu Glu Asp Leu Asn
            130                 135                 140

Gly Ala Ala Thr Val Glu Ser Cys Leu Ala Lys Pro His Thr Glu Asn
145                 150                 155                 160

Ser Phe Thr Asn Val
                165

<210> SEQ ID NO 16
<211> LENGTH: 165
<212> TYPE: PRT
<213> ORGANISM: Artificial sequence
<220> FEATURE:
<223> OTHER INFORMATION: Human single domain antibody

<400> SEQUENCE: 16

Leu Leu Leu Leu Ala Ala Gln Pro Ala Met Ala Glu Val Gln Leu Leu
1               5                   10                  15

Glu Ser Gly Gly Gly Leu Val Gln Pro Gly Gly Ser Leu Arg Leu Ser
            20                  25                  30

Cys Ala Ala Ser Gly Phe Arg Asp Ser Asp Glu Asp Met Gly Trp Val
            35                  40                  45

Arg Gln Ala Pro Gly Lys Gly Leu Glu Trp Val Ser Ser Ile Asn Ala
        50                  55                  60

Asn Asp Gly Ser Thr Tyr Tyr Ala Asp Ser Val Lys Gly Arg Phe Thr
65                  70                  75                  80

Ile Ser Arg Asp Asn Ser Lys Asn Thr Leu Tyr Leu Gln Met Asn Ser
            85                  90                  95

Leu Arg Ala Glu Asp Thr Ala Val Tyr Tyr Cys Ala Ser Gln Tyr Asp
            100                 105                 110

Asp Glu Phe Ala Phe Asp Tyr Trp Gly Gln Gly Thr Leu Val Thr Val
            115                 120                 125

Ser Ser Ala Ala Ala Glu Gln Lys Leu Ile Ser Glu Glu Asp Leu Asn
            130                 135                 140

Gly Ala Ala Thr Val Glu Ser Cys Leu Ala Lys Pro His Thr Glu Asn
145                 150                 155                 160

Ser Phe Thr Asn Val
                165

<210> SEQ ID NO 17
<211> LENGTH: 165
<212> TYPE: PRT
<213> ORGANISM: Artificial sequence
<220> FEATURE:
<223> OTHER INFORMATION: Human single domain antibody

<400> SEQUENCE: 17

Leu Leu Leu Leu Ala Ala Gln Pro Ala Met Ala Glu Val Gln Leu Leu
1               5                   10                  15

Glu Ser Gly Gly Gly Leu Val Gln Pro Gly Gly Ser Leu Arg Leu Ser
            20                  25                  30

Cys Ala Ala Ser Gly Phe Arg Asp Ser Asp Glu Asp Met Gly Trp Val
            35                  40                  45
```

```
Arg Gln Ala Pro Gly Lys Gly Leu Glu Trp Val Ser Ser Ile Gly Asn
         50                  55                  60

Tyr Asn Gly Ser Thr Tyr Tyr Ala Asp Ser Val Lys Gly Arg Phe Thr
65                  70                  75                  80

Ile Ser Arg Asp Asn Ser Lys Asn Thr Leu Tyr Leu Gln Met Asn Ser
                85                  90                  95

Leu Arg Ala Glu Asp Thr Ala Val Tyr Tyr Cys Ala Ser Val Ser Asp
            100                 105                 110

Ser Gly Phe Ser Phe Asp Tyr Trp Gly Gln Gly Thr Leu Val Thr Val
        115                 120                 125

Ser Ser Ala Ala Ala Glu Gln Lys Leu Ile Ser Glu Glu Asp Leu Asn
        130                 135                 140

Gly Ala Ala Thr Val Glu Ser Cys Leu Ala Lys Pro His Thr Glu Asn
145                 150                 155                 160

Ser Phe Thr Asn Val
                165

<210> SEQ ID NO 18
<211> LENGTH: 165
<212> TYPE: PRT
<213> ORGANISM: Artificial sequence
<220> FEATURE:
<223> OTHER INFORMATION: Human single domain antibody

<400> SEQUENCE: 18

Leu Leu Leu Leu Ala Ala Gln Pro Ala Met Ala Glu Val Gln Leu Leu
1               5                   10                  15

Glu Ser Gly Gly Gly Leu Val Gln Pro Gly Gly Ser Leu Arg Leu Ser
                20                  25                  30

Cys Ala Ala Ser Gly Phe Arg Asp Ser Asp Glu Asp Met Gly Trp Val
            35                  40                  45

Arg Gln Ala Pro Gly Lys Gly Leu Glu Trp Val Ser Ser Ile Tyr Gly
        50                  55                  60

Pro Ser Gly Ser Thr Tyr Tyr Ala Asp Ser Val Lys Gly Arg Phe Thr
65                  70                  75                  80

Ile Ser Arg Asp Asn Ser Lys Asn Thr Leu Tyr Leu Gln Met Asn Ser
                85                  90                  95

Leu Arg Ala Glu Asp Thr Ala Val Tyr Tyr Cys Ala Ser Ser Asp Trp
            100                 105                 110

Asp Gly Tyr Ser Phe Asp Tyr Trp Gly Gln Gly Thr Leu Val Thr Val
        115                 120                 125

Ser Ser Ala Ala Ala Glu Gln Lys Leu Ile Ser Glu Glu Asp Leu Asn
        130                 135                 140

Gly Ala Ala Thr Val Glu Ser Cys Leu Ala Lys Pro His Thr Glu Asn
145                 150                 155                 160

Ser Phe Thr Asn Val
                165

<210> SEQ ID NO 19
<211> LENGTH: 165
<212> TYPE: PRT
<213> ORGANISM: Artificial sequence
<220> FEATURE:
<223> OTHER INFORMATION: Human single domain antibody

<400> SEQUENCE: 19

Leu Leu Leu Leu Ala Ala Gln Pro Ala Met Ala Glu Val Gln Leu Leu
```

```
1               5                   10                  15
Glu Ser Gly Gly Gly Leu Val Gln Pro Gly Gly Ser Leu Arg Leu Ser
            20                  25                  30
Cys Ala Ala Ser Gly Phe Arg Asp Ser Asp Glu Asp Met Gly Trp Val
            35                  40                  45
Arg Gln Ala Pro Gly Lys Gly Leu Glu Trp Val Ser Ser Ile Asp Ala
            50                  55                  60
Glu Asp Gly Ser Thr Tyr Tyr Ala Asp Ser Val Lys Gly Arg Phe Thr
65                  70                  75                  80
Ile Ser Arg Asp Asn Ser Lys Asn Thr Leu Tyr Leu Gln Met Asn Ser
                85                  90                  95
Leu Arg Ala Glu Asp Thr Ala Val Tyr Tyr Cys Ala Ser Gln Asp Gly
            100                 105                 110
Ala Tyr Tyr Thr Phe Asp Tyr Trp Gly Gln Gly Thr Leu Val Thr Val
            115                 120                 125
Ser Ser Ala Ala Ala Glu Gln Lys Leu Ile Ser Glu Glu Asp Leu Asn
            130                 135                 140
Gly Ala Ala Thr Val Glu Ser Cys Leu Ala Lys Pro His Thr Glu Asn
145                 150                 155                 160
Ser Phe Thr Asn Val
            165
```

<210> SEQ ID NO 20
<211> LENGTH: 9
<212> TYPE: PRT
<213> ORGANISM: Artificial sequence
<220> FEATURE:
<223> OTHER INFORMATION: CDR sequence

<400> SEQUENCE: 20

```
Phe Arg Asp Ser Asp Glu Asp Met Gly
1               5
```

<210> SEQ ID NO 21
<211> LENGTH: 15
<212> TYPE: PRT
<213> ORGANISM: Artificial sequence
<220> FEATURE:
<223> OTHER INFORMATION: CDR sequence

<400> SEQUENCE: 21

```
Ser Ile Gly Asp Glu Ser Gly Ser Thr Tyr Tyr Ala Asp Ser Val
1               5                   10                  15
```

<210> SEQ ID NO 22
<211> LENGTH: 10
<212> TYPE: PRT
<213> ORGANISM: Artificial sequence
<220> FEATURE:
<223> OTHER INFORMATION: CDR sequence

<400> SEQUENCE: 22

```
Thr Ser Asp Ser Tyr Trp Ser Phe Asp Tyr
1               5                   10
```

<210> SEQ ID NO 23
<211> LENGTH: 15
<212> TYPE: PRT
<213> ORGANISM: Artificial sequence
<220> FEATURE:
<223> OTHER INFORMATION: CDR sequence

```
<400> SEQUENCE: 23

Ser Ile Asn Ala Pro Asp Gly Ser Thr Tyr Tyr Ala Asp Ser Val
1               5                   10                  15

<210> SEQ ID NO 24
<211> LENGTH: 10
<212> TYPE: PRT
<213> ORGANISM: Artificial sequence
<220> FEATURE:
<223> OTHER INFORMATION: CDR sequence

<400> SEQUENCE: 24

Gln Trp Asp Asp Gly Tyr Ala Phe Asp Tyr
1               5                   10

<210> SEQ ID NO 25
<211> LENGTH: 15
<212> TYPE: PRT
<213> ORGANISM: Artificial sequence
<220> FEATURE:
<223> OTHER INFORMATION: CDR sequence

<400> SEQUENCE: 25

Ser Ile Ser Gly Ser Asp Gly Ser Thr Tyr Tyr Ala Asp Ser Val
1               5                   10                  15

<210> SEQ ID NO 26
<211> LENGTH: 10
<212> TYPE: PRT
<213> ORGANISM: Artificial sequence
<220> FEATURE:
<223> OTHER INFORMATION: CDR sequence

<400> SEQUENCE: 26

Thr Asp Tyr Leu Arg Ser Ser Phe Asp Tyr
1               5                   10

<210> SEQ ID NO 27
<211> LENGTH: 15
<212> TYPE: PRT
<213> ORGANISM: Artificial sequence
<220> FEATURE:
<223> OTHER INFORMATION: CDR sequence

<400> SEQUENCE: 27

Ser Ile Asn Asn Ser Gly Gly Ser Thr Tyr Tyr Ala Asp Ser Val
1               5                   10                  15

<210> SEQ ID NO 28
<211> LENGTH: 10
<212> TYPE: PRT
<213> ORGANISM: Artificial sequence
<220> FEATURE:
<223> OTHER INFORMATION: CDR sequence

<400> SEQUENCE: 28

Thr Tyr Asp Trp Asn Tyr Ser Phe Asp Tyr
1               5                   10

<210> SEQ ID NO 29
<211> LENGTH: 15
<212> TYPE: PRT
<213> ORGANISM: Artificial sequence
<220> FEATURE:
<223> OTHER INFORMATION: CDR sequence

<400> SEQUENCE: 29
```

Ser Ile Ser Ala Glu Ser Gly Ser Thr Tyr Tyr Ala Asp Ser Val
1               5                   10                  15

<210> SEQ ID NO 30
<211> LENGTH: 10
<212> TYPE: PRT
<213> ORGANISM: Artificial sequence
<220> FEATURE:
<223> OTHER INFORMATION: CDR sequence

<400> SEQUENCE: 30

Gln Tyr Gly Ala Tyr His Asp Phe Asp Tyr
1               5                   10

<210> SEQ ID NO 31
<211> LENGTH: 15
<212> TYPE: PRT
<213> ORGANISM: Artificial sequence
<220> FEATURE:
<223> OTHER INFORMATION: CDR sequence

<400> SEQUENCE: 31

Ser Ile Asn Tyr Asn Ser Gly Ser Thr Tyr Tyr Ala Asp Ser Val
1               5                   10                  15

<210> SEQ ID NO 32
<211> LENGTH: 10
<212> TYPE: PRT
<213> ORGANISM: Artificial sequence
<220> FEATURE:
<223> OTHER INFORMATION: CDR sequence

<400> SEQUENCE: 32

Thr Pro Asn Leu Asn Ser Ser Phe Asp Tyr
1               5                   10

<210> SEQ ID NO 33
<211> LENGTH: 15
<212> TYPE: PRT
<213> ORGANISM: Artificial sequence
<220> FEATURE:
<223> OTHER INFORMATION: CDR sequence

<400> SEQUENCE: 33

Ser Ile Ser Asp Glu Asp Gly Ser Thr Tyr Tyr Ala Asp Ser Val
1               5                   10                  15

<210> SEQ ID NO 34
<211> LENGTH: 10
<212> TYPE: PRT
<213> ORGANISM: Artificial sequence
<220> FEATURE:
<223> OTHER INFORMATION: CDR sequence

<400> SEQUENCE: 34

Ser Gly Asp Trp Trp Tyr Gly Phe Asp Tyr
1               5                   10

<210> SEQ ID NO 35
<211> LENGTH: 15
<212> TYPE: PRT
<213> ORGANISM: Artificial sequence
<220> FEATURE:
<223> OTHER INFORMATION: CDR sequence

<400> SEQUENCE: 35

```
Ser Ile Ser Gly Glu Ser Gly Ser Thr Tyr Tyr Ala Asp Ser Val
1               5                   10                  15

<210> SEQ ID NO 36
<211> LENGTH: 10
<212> TYPE: PRT
<213> ORGANISM: Artificial sequence
<220> FEATURE:
<223> OTHER INFORMATION: CDR sequence

<400> SEQUENCE: 36

Val Asp Pro Leu Asp Thr Tyr Phe Asp Tyr
1               5                   10

<210> SEQ ID NO 37
<211> LENGTH: 15
<212> TYPE: PRT
<213> ORGANISM: Artificial sequence
<220> FEATURE:
<223> OTHER INFORMATION: CDR sequence

<400> SEQUENCE: 37

Ser Ile Gln Ser Ser Asp Gly Ser Thr Tyr Tyr Ala Asp Ser Val
1               5                   10                  15

<210> SEQ ID NO 38
<211> LENGTH: 10
<212> TYPE: PRT
<213> ORGANISM: Artificial sequence
<220> FEATURE:
<223> OTHER INFORMATION: CDR sequence

<400> SEQUENCE: 38

Ser Ser Gln Asn Gly Tyr Val Phe Asp Tyr
1               5                   10

<210> SEQ ID NO 39
<211> LENGTH: 15
<212> TYPE: PRT
<213> ORGANISM: Artificial sequence
<220> FEATURE:
<223> OTHER INFORMATION: CDR sequence

<400> SEQUENCE: 39

Ser Ile Asn Asn Glu Ser Gly Ser Thr Tyr Tyr Ala Asp Ser Val
1               5                   10                  15

<210> SEQ ID NO 40
<211> LENGTH: 10
<212> TYPE: PRT
<213> ORGANISM: Artificial sequence
<220> FEATURE:
<223> OTHER INFORMATION: CDR sequence

<400> SEQUENCE: 40

Thr Ser Tyr Tyr Gly Phe Asp Phe Asp Tyr
1               5                   10

<210> SEQ ID NO 41
<211> LENGTH: 15
<212> TYPE: PRT
<213> ORGANISM: Artificial sequence
<220> FEATURE:
<223> OTHER INFORMATION: CDR sequence

<400> SEQUENCE: 41

Ser Ile Tyr Ala Pro Asn Gly Ser Thr Tyr Tyr Ala Asp Ser Val
```

```
1               5                   10                  15
```

<210> SEQ ID NO 42
<211> LENGTH: 8
<212> TYPE: PRT
<213> ORGANISM: Artificial sequence
<220> FEATURE:
<223> OTHER INFORMATION: CDR sequence

<400> SEQUENCE: 42

```
Asn Thr Tyr Asp Ala Phe Asp Tyr
1               5
```

<210> SEQ ID NO 43
<211> LENGTH: 15
<212> TYPE: PRT
<213> ORGANISM: Artificial sequence
<220> FEATURE:
<223> OTHER INFORMATION: CDR sequence

<400> SEQUENCE: 43

```
Ser Ile Ala Ser Asp Ser Gly Ser Thr Tyr Tyr Ala Asp Ser Val
1               5                   10                  15
```

<210> SEQ ID NO 44
<211> LENGTH: 10
<212> TYPE: PRT
<213> ORGANISM: Artificial sequence
<220> FEATURE:
<223> OTHER INFORMATION: CDR sequence

<400> SEQUENCE: 44

```
Ser Gly Tyr Ala Gly Thr Val Phe Asp Tyr
1               5                   10
```

<210> SEQ ID NO 45
<211> LENGTH: 15
<212> TYPE: PRT
<213> ORGANISM: Artificial sequence
<220> FEATURE:
<223> OTHER INFORMATION: CDR sequence

<400> SEQUENCE: 45

```
Ser Ile Gly Ala Gly Ser Gly Ser Thr Tyr Tyr Ala Asp Ser Val
1               5                   10                  15
```

<210> SEQ ID NO 46
<211> LENGTH: 10
<212> TYPE: PRT
<213> ORGANISM: Artificial sequence
<220> FEATURE:
<223> OTHER INFORMATION: CDR sequence

<400> SEQUENCE: 46

```
Ser Thr Asp Ala Arg Trp Gln Phe Asp Tyr
1               5                   10
```

<210> SEQ ID NO 47
<211> LENGTH: 15
<212> TYPE: PRT
<213> ORGANISM: Artificial sequence
<220> FEATURE:
<223> OTHER INFORMATION: CDR sequence

<400> SEQUENCE: 47

```
Ser Ile Asn Ala Asn Asp Gly Ser Thr Tyr Tyr Ala Asp Ser Val
1               5                   10                  15
```

```
<210> SEQ ID NO 48
<211> LENGTH: 10
<212> TYPE: PRT
<213> ORGANISM: Artificial sequence
<220> FEATURE:
<223> OTHER INFORMATION: CDR sequence

<400> SEQUENCE: 48

Gln Tyr Asp Asp Glu Phe Ala Phe Asp Tyr
1               5                   10

<210> SEQ ID NO 49
<211> LENGTH: 15
<212> TYPE: PRT
<213> ORGANISM: Artificial sequence
<220> FEATURE:
<223> OTHER INFORMATION: CDR sequence

<400> SEQUENCE: 49

Ser Ile Gly Asn Tyr Asn Gly Ser Thr Tyr Tyr Ala Asp Ser Val
1               5                   10                  15

<210> SEQ ID NO 50
<211> LENGTH: 10
<212> TYPE: PRT
<213> ORGANISM: Artificial sequence
<220> FEATURE:
<223> OTHER INFORMATION: CDR sequence

<400> SEQUENCE: 50

Val Ser Asp Ser Gly Phe Ser Phe Asp Tyr
1               5                   10

<210> SEQ ID NO 51
<211> LENGTH: 15
<212> TYPE: PRT
<213> ORGANISM: Artificial sequence
<220> FEATURE:
<223> OTHER INFORMATION: CDR sequence

<400> SEQUENCE: 51

Ser Ile Tyr Gly Pro Ser Gly Ser Thr Tyr Tyr Ala Asp Ser Val
1               5                   10                  15

<210> SEQ ID NO 52
<211> LENGTH: 10
<212> TYPE: PRT
<213> ORGANISM: Artificial sequence
<220> FEATURE:
<223> OTHER INFORMATION: CDR sequence

<400> SEQUENCE: 52

Ser Asp Trp Asp Gly Tyr Ser Phe Asp Tyr
1               5                   10

<210> SEQ ID NO 53
<211> LENGTH: 15
<212> TYPE: PRT
<213> ORGANISM: Artificial sequence
<220> FEATURE:
<223> OTHER INFORMATION: CDR sequence

<400> SEQUENCE: 53

Ser Ile Asp Ala Glu Asp Gly Ser Thr Tyr Tyr Ala Asp Ser Val
1               5                   10                  15
```

```
<210> SEQ ID NO 54
<211> LENGTH: 10
<212> TYPE: PRT
<213> ORGANISM: Artificial sequence
<220> FEATURE:
<223> OTHER INFORMATION: CDR sequence

<400> SEQUENCE: 54

Gln Asp Gly Ala Tyr Tyr Thr Phe Asp Tyr
1               5                   10

<210> SEQ ID NO 55
<211> LENGTH: 15
<212> TYPE: PRT
<213> ORGANISM: Artificial sequence
<220> FEATURE:
<223> OTHER INFORMATION: CDR sequence
<220> FEATURE:
<221> NAME/KEY: MISC_FEATURE
<222> LOCATION: (3)..(3)
<223> OTHER INFORMATION: X is Q, S, N, D, G, E or Y
<220> FEATURE:
<221> NAME/KEY: MISC_FEATURE
<222> LOCATION: (4)..(4)
<223> OTHER INFORMATION: X is S, G, N, A, D or Y
<220> FEATURE:
<221> NAME/KEY: MISC_FEATURE
<222> LOCATION: (5)..(5)
<223> OTHER INFORMATION: X is S, E, N, Y, G, D or P
<220> FEATURE:
<221> NAME/KEY: MISC_FEATURE
<222> LOCATION: (6)..(6)
<223> OTHER INFORMATION: X is D, G, S or N

<400> SEQUENCE: 55

Ser Ile Xaa Xaa Xaa Xaa Gly Ser Thr Tyr Tyr Ala Asp Ser Val
1               5                   10                  15

<210> SEQ ID NO 56
<211> LENGTH: 11
<212> TYPE: PRT
<213> ORGANISM: Artificial sequence
<220> FEATURE:
<223> OTHER INFORMATION: CDR sequence

<400> SEQUENCE: 56

Ser Ile Ser Thr Ser Asp Gly Ser Thr Tyr Tyr
1               5                   10

<210> SEQ ID NO 57
<211> LENGTH: 10
<212> TYPE: PRT
<213> ORGANISM: Artificial sequence
<220> FEATURE:
<223> OTHER INFORMATION: CDR sequence

<400> SEQUENCE: 57

Gln Tyr Asp Thr Gly Tyr Ser Phe Asp Tyr
1               5                   10

<210> SEQ ID NO 58
<211> LENGTH: 227
<212> TYPE: PRT
<213> ORGANISM: Homo sapiens

<400> SEQUENCE: 58

Asp Lys Thr His Thr Cys Pro Pro Cys Pro Ala Pro Glu Leu Leu Gly
1               5                   10                  15
```

```
Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Lys
225

<210> SEQ ID NO 59
<211> LENGTH: 223
<212> TYPE: PRT
<213> ORGANISM: Homo sapiens

<400> SEQUENCE: 59

Val Glu Cys Pro Pro Cys Pro Ala Pro Pro Val Ala Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Gln Phe Asn Trp Tyr Val Asp Gly Met Glu Val His Asn Ala Lys
50                  55                  60

Thr Lys Pro Arg Glu Glu Gln Phe Asn Ser Thr Phe Arg Val Val Ser
65                  70                  75                  80

Val Leu Thr Val Val His Gln Asp Trp Leu Asn Gly Lys Glu Tyr Lys
                85                  90                  95

Cys Lys Val Ser Asn Lys Gly Leu Pro Ala Pro Ile Glu Lys Thr Ile
            100                 105                 110

Ser Lys Thr Lys Gly Gln Pro Arg Glu Pro Gln Val Tyr Thr Leu Pro
        115                 120                 125

Pro Ser Arg Glu Glu Met Thr Lys Asn Gln Val Ser Leu Thr Cys Leu
130                 135                 140

Val Lys Gly Phe Tyr Pro Ser Asp Ile Ala Val Glu Trp Glu Ser Asn
145                 150                 155                 160
```

```
Gly Gln Pro Glu Asn Asn Tyr Lys Thr Thr Pro Pro Met Leu Asp Ser
            165             170                 175

Asp Gly Ser Phe Phe Leu Tyr Ser Lys Leu Thr Val Asp Lys Ser Arg
            180             185                 190

Trp Gln Gln Gly Asn Val Phe Ser Cys Ser Val Met His Glu Ala Leu
        195             200             205

His Asn His Tyr Thr Gln Lys Ser Leu Ser Leu Ser Pro Gly Lys
    210             215             220
```